(12) United States Patent
Kovarik

(10) Patent No.: US 9,445,936 B2
(45) Date of Patent: Sep. 20, 2016

(54) METHOD OF TREATING SNORING AND OBSTRUCTIVE SLEEP APNEA

(71) Applicant: Joseph E. Kovarik, Englewood, CO (US)

(72) Inventor: Joseph E. Kovarik, Englewood, CO (US)

( * ) Notice: Subject to any disclaimer, the term of this patent is extended or adjusted under 35 U.S.C. 154(b) by 327 days.

(21) Appl. No.: 14/225,503

(22) Filed: Mar. 26, 2014

(65) Prior Publication Data

US 2014/0238411 A1 Aug. 28, 2014

Related U.S. Application Data

(63) Continuation of application No. 13/367,052, filed on Feb. 6, 2012, now Pat. No. 8,701,671.

(60) Provisional application No. 61/439,652, filed on Feb. 4, 2011, provisional application No. 61/556,023, filed on Nov. 4, 2011.

(51) Int. Cl.
*A61F 5/56* (2006.01)

(52) U.S. Cl.
CPC ..................... *A61F 5/566* (2013.01)

(58) Field of Classification Search
CPC ....................................... A61F 5/566
USPC ...... 128/846, 848, 859–862; 602/902; 2/455
See application file for complete search history.

(56) References Cited

U.S. PATENT DOCUMENTS

| 1,492,600 A | 5/1924 | Laskey |
|---|---|---|
| 3,640,741 A | 2/1972 | Etes |
| 3,832,460 A | 8/1974 | Kosti |
| 3,996,934 A | 12/1976 | Zaffaroni |
| 4,136,145 A | 1/1979 | Fuchs et al. |
| 4,136,162 A | 1/1979 | Fuchs et al. |
| 4,163,777 A | 8/1979 | Mitra |
| 4,226,848 A | 10/1980 | Nagai et al. |
| 4,250,163 A | 2/1981 | Nagai et al. |
| 4,285,934 A | 8/1981 | Tinnell |
| 4,286,592 A | 9/1981 | Chandrasekaran |

(Continued)

FOREIGN PATENT DOCUMENTS

| DE | 4412190 | 10/1995 |
|---|---|---|
| EP | 410696 | 1/1991 |

(Continued)

OTHER PUBLICATIONS

Agrawal et al., "Technique to control pH in vicinity of biodegrading PLA-PGA implants," J. Biomed. Mater Res., 1997, vol. 38(2), pp. 105-114, Abstract, 2 pages.

(Continued)

*Primary Examiner* — Michael Brown
(74) *Attorney, Agent, or Firm* — Sheridan Ross P.C.

(57) ABSTRACT

A method, system and device for addressing the reduction of snoring includes a removable or dissolvable strip of material that adhere to mucosal tissue of a person's soft palate to provide stiffening support therefore, thus reducing the occurrence of vibration of such tissue during sleep. Preferred embodiments include of a specially textured surface, either one both or at least the outer side of an adhesive strip (the side facing away from the mucosal tissue to which it is attached) that has anti-microbial characteristics, biolumines-cent expressions, etc. and a surface topography that resists bioadhesion of undesired bacteria that are typically present in a human's mouth.

20 Claims, 9 Drawing Sheets

(56) References Cited

U.S. PATENT DOCUMENTS

| | | | |
|---|---|---|---|
| 4,292,299 A | 9/1981 | Suzuki et al. |
| 4,381,296 A | 4/1983 | Tinnell |
| 4,517,173 A | 5/1985 | Kizawa et al. |
| 4,518,721 A | 5/1985 | Dhabhar et al. |
| 4,572,832 A | 2/1986 | Kigasawa et al. |
| 4,668,232 A | 5/1987 | Cordes et al. |
| 4,713,243 A | 12/1987 | Schiraldi et al. |
| 4,715,369 A | 12/1987 | Suzuki et al. |
| 4,740,365 A | 4/1988 | Yukimatsu et al. |
| 4,765,983 A | 8/1988 | Takayanagi et al. |
| 4,830,008 A | 5/1989 | Meer |
| 4,849,246 A | 7/1989 | Schmidt |
| 4,867,970 A | 9/1989 | Newsham et al. |
| 4,889,720 A | 12/1989 | Konishi |
| 4,894,232 A | 1/1990 | Reul et al. |
| 4,900,554 A | 2/1990 | Yanagibashi et al. |
| 4,906,463 A | 3/1990 | Cleary et al. |
| 4,915,948 A | 4/1990 | Gallopo et al. |
| 5,002,970 A | 3/1991 | Eby, III |
| 5,059,189 A | 10/1991 | Cilento et al. |
| 5,064,654 A | 11/1991 | Berner et al. |
| 5,081,157 A | 1/1992 | Pomerantz |
| 5,081,158 A | 1/1992 | Pomerantz |
| 5,116,621 A | 5/1992 | Oji et al. |
| 5,137,729 A | 8/1992 | Kuroya et al. |
| 5,158,789 A | 10/1992 | DuRoss |
| 5,166,233 A | 11/1992 | Kuroya et al. |
| 5,190,053 A | 3/1993 | Meer |
| 5,192,802 A | 3/1993 | Rencher |
| 5,196,202 A | 3/1993 | Konishi |
| 5,284,161 A | 2/1994 | Karell |
| 5,298,258 A | 3/1994 | Akemi et al. |
| 5,314,915 A | 5/1994 | Rencher |
| 5,332,576 A | 7/1994 | Mantelle |
| 5,462,749 A | 10/1995 | Rencher |
| 5,465,734 A | 11/1995 | Alvarez et al. |
| 5,466,465 A | 11/1995 | Royds et al. |
| 5,505,956 A | 4/1996 | Kim et al. |
| 5,578,315 A | 11/1996 | Chien et al. |
| 5,629,003 A | 5/1997 | Horstmann et al. |
| 5,643,603 A | 7/1997 | Bottenberg et al. |
| 5,713,852 A | 2/1998 | Anthony et al. |
| 5,718,702 A | 2/1998 | Edwards |
| 5,719,196 A | 2/1998 | Uhari et al. |
| 5,792,067 A | 8/1998 | Karell |
| 5,800,832 A | 9/1998 | Tapolsky et al. |
| 5,804,211 A | 9/1998 | Robertson et al. |
| 5,843,021 A | 12/1998 | Edwards et al. |
| 5,855,872 A | 1/1999 | Libin |
| 5,895,804 A | 4/1999 | Lee et al. |
| 5,900,245 A | 5/1999 | Sawhney et al. |
| 5,948,430 A | 9/1999 | Zerbe et al. |
| 5,988,171 A | 11/1999 | Sohn et al. |
| 6,054,143 A | 4/2000 | Jones |
| 6,072,100 A | 6/2000 | Mooney et al. |
| 6,139,861 A | 10/2000 | Friedman |
| 6,161,541 A | 12/2000 | Woodson |
| 6,174,546 B1 | 1/2001 | Therriault et al. |
| 6,210,699 B1 | 4/2001 | Acharya et al. |
| 6,250,307 B1 | 6/2001 | Conrad et al. |
| 6,284,235 B1 | 9/2001 | Foreman et al. |
| 6,352,711 B1 | 3/2002 | Campbell |
| 6,375,963 B1 | 4/2002 | Repka et al. |
| 6,390,096 B1 * | 5/2002 | Conrad .................... A61F 2/00 128/848 |
| 6,431,174 B1 | 8/2002 | Knudson et al. |
| 6,432,986 B2 | 8/2002 | Levin |
| 6,439,238 B1 | 8/2002 | Brenzel et al. |
| 6,458,380 B1 | 10/2002 | Leaderman |
| 6,458,777 B1 | 10/2002 | Sonis et al. |
| 6,467,485 B1 | 10/2002 | Schmidt |
| 6,502,574 B2 | 1/2003 | Stevens et al. |
| 6,509,028 B2 | 1/2003 | Williams et al. |
| 6,523,542 B2 * | 2/2003 | Knudson ................ A61F 2/00 128/897 |
| 6,552,024 B1 | 4/2003 | Chen et al. |
| 6,555,125 B2 | 4/2003 | Campbell |
| 6,578,580 B2 * | 6/2003 | Conrad ..................... A61F 2/00 128/848 |
| 6,585,997 B2 | 7/2003 | Moro et al. |
| 6,599,883 B1 | 7/2003 | Romeo et al. |
| 6,620,846 B1 | 9/2003 | Jonn et al. |
| 6,713,463 B2 | 3/2004 | Sonis et al. |
| 6,726,920 B1 | 4/2004 | Theeuwes et al. |
| 6,734,157 B2 | 5/2004 | Radwanski et al. |
| 6,748,951 B1 | 6/2004 | Schmidt |
| 6,794,318 B2 | 9/2004 | Anderson et al. |
| 6,803,420 B2 | 10/2004 | Cleary et al. |
| 6,916,480 B2 | 7/2005 | Anderson et al. |
| 6,919,373 B1 | 7/2005 | Lam et al. |
| 6,923,981 B2 | 8/2005 | Leung et al. |
| 7,001,609 B1 | 2/2006 | Matson et al. |
| 7,067,116 B1 | 6/2006 | Bess et al. |
| 7,087,249 B2 | 8/2006 | Burrell et al. |
| 7,097,853 B1 | 8/2006 | Garbe et al. |
| 7,138,135 B2 | 11/2006 | Chen et al. |
| 7,143,709 B2 | 12/2006 | Brennan et al. |
| 7,146,981 B2 | 12/2006 | Knudson et al. |
| 7,276,246 B2 | 10/2007 | Zhang |
| 7,287,646 B2 | 10/2007 | Gierskcky |
| 7,306,812 B2 | 12/2007 | Zhang |
| 7,332,230 B1 | 2/2008 | Krumme |
| 7,357,891 B2 | 4/2008 | Yang et al. |
| 7,425,292 B2 | 9/2008 | Yang et al. |
| 7,470,397 B2 | 12/2008 | Meathrel et al. |
| 7,500,484 B2 | 3/2009 | Nelson et al. |
| 7,566,310 B2 | 7/2009 | Badr et al. |
| 7,575,739 B2 | 8/2009 | Tamarkin et al. |
| 7,579,019 B2 | 8/2009 | Tapolsky et al. |
| 7,579,078 B2 | 8/2009 | Hartmann et al. |
| 7,615,235 B2 | 11/2009 | Rademacher et al. |
| 7,632,525 B2 | 12/2009 | Dodds et al. |
| 7,645,803 B2 | 1/2010 | Tamarkin et al. |
| 7,648,712 B2 | 1/2010 | Bess et al. |
| 7,650,848 B2 | 1/2010 | Brennan et al. |
| 7,666,502 B2 | 2/2010 | Magill et al. |
| 7,669,603 B2 | 3/2010 | Knudson et al. |
| 7,686,021 B2 | 3/2010 | Knudson et al. |
| 7,704,518 B2 | 4/2010 | Tamarkin et al. |
| 7,727,466 B2 | 6/2010 | Meathrel et al. |
| 7,799,337 B2 | 9/2010 | Levin |
| 7,820,145 B2 | 10/2010 | Tamarkin et al. |
| 7,824,588 B2 | 11/2010 | Yang et al. |
| 7,824,704 B2 | 11/2010 | Anderson et al. |
| 7,845,356 B2 | 12/2010 | Paraschac et al. |
| 7,906,140 B2 | 3/2011 | Bromley et al. |
| 7,937,159 B2 | 5/2011 | Lima et al. |
| 7,984,714 B2 | 7/2011 | Hausmann et al. |
| 7,992,566 B2 | 8/2011 | Pflueger et al. |
| 7,997,266 B2 | 8/2011 | Frazier et al. |
| 8,104,478 B2 | 1/2012 | Pflueger et al. |
| 8,383,201 B2 | 2/2013 | Berry et al. |
| 8,657,879 B2 | 2/2014 | Shalon et al. |
| 8,701,671 B2 * | 4/2014 | Kovarik .................. A61F 5/566 128/848 |
| 8,865,211 B2 | 10/2014 | Tzannis et al. |
| 8,999,372 B2 | 4/2015 | Davidson et al. |
| 9,017,718 B2 | 4/2015 | Tan et al. |
| 2002/0022057 A1 | 2/2002 | Battey et al. |
| 2002/0037310 A1 | 3/2002 | Jonn et al. |
| 2003/0031737 A1 | 2/2003 | Rosenbloom |
| 2003/0104041 A1 | 6/2003 | Hsu et al. |
| 2003/0106243 A1 | 6/2003 | Tucker |
| 2003/0124178 A1 | 7/2003 | Haley |
| 2003/0140930 A1 | 7/2003 | Knudson et al. |
| 2003/0149387 A1 | 8/2003 | Barakat et al. |
| 2003/0149445 A1 | 8/2003 | Knudson et al. |
| 2004/0096569 A1 | 5/2004 | Barkalow et al. |
| 2004/0120991 A1 | 6/2004 | Gardner et al. |
| 2004/0136923 A1 | 7/2004 | Davidson et al. |
| 2004/0180080 A1 | 9/2004 | Furusawa et al. |
| 2004/0228804 A1 | 11/2004 | Jones et al. |
| 2005/0004417 A1 | 1/2005 | Nelson et al. |
| 2005/0159637 A9 | 7/2005 | Nelson et al. |

(56) References Cited

U.S. PATENT DOCUMENTS

| | | |
|---|---|---|
| 2005/0196358 A1 | 9/2005 | Georgiades et al. |
| 2006/0035008 A1 | 2/2006 | Virgallito et al. |
| 2006/0064903 A1 | 3/2006 | Tucker |
| 2006/0188813 A1 | 8/2006 | Shimada |
| 2006/0204591 A1 | 9/2006 | Burrel et al. |
| 2006/0207721 A1 | 9/2006 | Slominski et al. |
| 2007/0102010 A1 | 5/2007 | Lemperle et al. |
| 2007/0202057 A1 | 8/2007 | Fankhauser et al. |
| 2007/0218114 A1 | 9/2007 | Duggan |
| 2007/0227545 A1 | 10/2007 | Conrad et al. |
| 2007/0246052 A1 | 10/2007 | Hegde et al. |
| 2007/0261701 A1 | 11/2007 | Sanders |
| 2007/0293587 A1 | 12/2007 | Haley |
| 2007/0295340 A1 | 12/2007 | Buscemi |
| 2008/0075825 A1 | 3/2008 | Fuisz et al. |
| 2009/0098192 A1 | 4/2009 | Fuisz |
| 2009/0196907 A1 | 8/2009 | Bunick et al. |
| 2009/0196908 A1 | 8/2009 | Lee et al. |
| 2010/0040593 A1 | 2/2010 | Hedman et al. |
| 2010/0040712 A1 | 2/2010 | Fisher |
| 2010/0229876 A1 | 9/2010 | Knudson et al. |
| 2010/0285098 A1 | 11/2010 | Haley |
| 2011/0009834 A1 | 1/2011 | Asmussen et al. |
| 2011/0033542 A1 | 2/2011 | Myers et al. |
| 2011/0088701 A1 | 4/2011 | Thornton |
| 2011/0100378 A1 | 5/2011 | Rousseau |
| 2011/0142942 A1 | 6/2011 | Schobel et al. |
| 2011/0230587 A1 | 9/2011 | MacInnis et al. |
| 2011/0230727 A1 | 9/2011 | Sanders et al. |
| 2011/0250626 A1 | 10/2011 | Williams et al. |
| 2011/0274795 A1 | 11/2011 | Bogue et al. |
| 2012/0222685 A1* | 9/2012 | Kovarik ............... A61F 5/566 128/848 |
| 2013/0087155 A1* | 4/2013 | Hedman ............... A61F 5/566 128/848 |
| 2014/0199266 A1 | 7/2014 | Park et al. |
| 2014/0271867 A1 | 9/2014 | Myers et al. |
| 2014/0333003 A1 | 11/2014 | Allen et al. |
| 2014/0356460 A1 | 12/2014 | Lutin |
| 2015/0038594 A1 | 2/2015 | Borges et al. |
| 2015/0150792 A1 | 6/2015 | Klingman |
| 2015/0290026 A1* | 10/2015 | Kovarik ............... A61F 5/566 128/848 |

FOREIGN PATENT DOCUMENTS

| | | |
|---|---|---|
| JP | S56-100714 | 8/1981 |
| WO | WO 98/22097 | 5/1998 |
| WO | WO 2008/097890 | 8/2008 |
| WO | WO 2009/052421 | 4/2009 |

OTHER PUBLICATIONS

Athanasiou et al., "In vitro degradation and release characteristics of biodegradable implants containing trypsin inhibitor," Clin. Orthop. Relat. Res., 1995, vol. 315, pp. 272-281, Abstract, 2 pages.

Blumen et al., "Radiofrequency ablation for the treatment of mild to moderate obstructive sleep apnea," Laryngoscope, 2002, vol. 112(11), pp. 2086-2092, Abstract, 2 pages.

Brietzke et al., "Injection snoreplasty: how to treat snoring without all the pain and expense," Otolaryngol Head Neck Surg, 2001, vol. 124(5), pp. 503-510, Abstract, 2 pages.

Brietzke et al., "Injection snoreplasty: extended follow-up and new objective data," Otolaryngol Head Neck Surg, 2003, vol. 128(5), pp. 605-615, Abstract, 2 pages.

Brietzke et al., "Injection snoreplasty: investigation of alternative sclerotherapy agents," Otolaryngol Head Neck Surg, 2004, vol. 130(1), pp. 47-57, Abstract, 2 pages.

Catalano et al., "Additional palatal implants for refractory snoring," Otolaryngol Head Neck Surg, 2007, vol. 137(1), pp. 105-109, Abstract, 2 pages.

Charulatha et al., "Influence of different crosslinking treatments on the physical properties of collagen membranes," Biomaterials, 2003, vol. 24(5), pp. 759-767, Abstract, 2 pages.

Chuang et al., "Effects of exogenous crosslinking on in vitro tensile and compressive moduli of lumbar intervertebral discs," Clin. Biomech (Bristol. Avon), 2007, vol. 22(1), pp. 14-20, Abstract, 2 pages.

Fischer et al., "[Radiofrequency ablation of the soft palate (somnoplasty). A new method in the treatment of habitual and obstructive snoring]," HNO, 2000, vol. 48, pp. 33-40, Abstract, 2 pages.

Friedman et al., "Patient selection and efficacy of pillar implant technique for treatment of snoring and obstructive sleep apnea/hypopnea syndrome," Otolaryngol Head Neck Surg, 2006, vol. 134, pp. 187-196, Abstract, 2 pages.

Gratzer et al., "Control of pH alters the type of cross-linking produced by 1-ethyl-3-(3-dimethylaminopropyl)-carbodiimide (EDC) treatment of acellular matrix vascular grafts," J. Biomed. Mater. Res., 2001, vol. 58(2), pp. 172-179, Abstract, 2 pages.

Guilleminault et al., "Snoring (I). Daytime sleepiness in regular heavy snorers," Chest, 1991, vol. 99, pp. 40-48.

Guilleminault et al., "The sleep apnea syndromes," Ann. Rev. Med., 1976, vol. 27, pp. 465-484, 1st page.

Han et al., "Proanthocyanidin: a natural crosslinking reagent for stabilizing collagen matrices," J. Biomed Mater. Res. A, 2003, vol. 65(1), pp. 118-124, Abstract, 2 pages.

Hedman et al., "Exogenous cross-linking increases the stability of spinal motion segments," Spine, 2006, vol. 31(15), pp. E480-485, Abstract, 2 pages.

Hoffman et al., "Glutaraldehyde and oxidised dextran as crosslinker reagents for chitosan-based scaffolds for cartilage tissue engineering," J. Mater. Sci. Mater. Med., 2009, vol. 20, 9 pages.

Hunter et al., "Meniscal material properties are minimally affected by matrix stabilization using glutaraldehyde and glycation with ribose," J. Ortho. Res., 2005, vol. 23, pp. 555-561.

Klapperich et al., "A novel biocompatible adhesive incorporating plant-derived monomers," J. Biomed Mater. Res., 2009, vol. 91(2), pp. 378-384, Abstract, 2 pages.

Yamamura et al. "Oral mucosal adhesive Film containing local anesthetics: in vitro and clinical evaluation." Journal of Biomedical Materials Research, Fall 1998, vol. 43, No. 3, pp. 313-317 (Abstract Only).

Official Action for U.S. Appl. No. 13/367,052 mailed Jan. 16, 2014, 8 pages.

Notice of Allowance for U.S. Appl. No. 13/367,052 mailed Feb. 24, 2014, 5 pages.

* cited by examiner

METHOD OF TREATING SNORING AND OBSTRUCTIVE SLEEP APNEA

RELATED APPLICATIONS

This application is a continuation of U.S. patent application Ser. No. 13/367,052, filed on Feb. 6, 2012, and claims priority from U.S. Provisional Patent Application Ser. No. 61/439,652 filed on Feb. 4, 2011 and U.S. Provisional Patent Application Ser. No. 61/556,023 filed Nov. 4, 2011. The entire disclosure of the prior applications are considered to be part of the disclosure of the accompanying application and are hereby incorporated by reference

FIELD OF THE INVENTION

The present invention is directed to a method, system and device for addressing the reduction of snoring and in particular, is directed to the use of dissolvable strips of material that adhere to mucosal tissue of a person's soft palate to provide stiffening support therefore, thus reducing the occurrence of vibration of such tissue during sleep.

BACKGROUND OF THE INVENTION

Snoring is a problem suffered by a large number of people. Snoring, upper airway resistance syndrome and obstructive sleep apnea syndrome (OSAS) are all breathing disorders related to narrowing of the upper airway during sleep. Individuals over age 65 experience such sleep difficulties, and the prevalence of sleep problems will therefore increase as the over-65 population increases. Each year, sleep disorders, sleep deprivation, and excessive daytime sleepiness add billions of dollars annually to the cost of health care and in lost productivity. When the muscles at the base of the tongue and the uvula (the small fleshy tissue hanging from the center of the back of the throat) relax and sag, the relaxed tissues may vibrate as air flows past the tissues during breathing, resulting in snoring. Snoring affects about half of men and 25 percent of women—most of whom are age 50 or older.

Snoring is a common chronic medical problem that is associated with episodic partial upper airway obstruction during sleep. Snoring afflicts millions of people worldwide. Snoring can lead to chronic fatigue that follows sleep deprivation and is considered by many to be a serious medical problem. The sound of snoring is produced by turbulent air-flow moving through an area of partial upper airway obstruction that produces resonant vibrations in the soft tissues adjacent to the upper airway. In many cases, snoring is caused by the relaxation of the tongue and the resulting blockage of the breathing airway. When the tongue of the sleeping individual relaxes and creates such a blockage and the individual subsequently forcibly passes air through the breathing airway, loud vibrations between the tongue and surrounding tissues will often result in the noises commonly referred to as snoring. Snoring is created by the vibration of the pharyngeal soft tissues as air passes through an airway that is too small to allow for smooth, unimpeded flow.

A percentage of those who snore also suffer from sleep apnea. The most common type of sleep apnea, obstructive sleep apnea (OSA), is caused by repeated collapse of soft tissues forming the walls of the upper airway in the subglottal region during sleep. Currently accepted treatment for OSA typically includes continuous positive airway pressure (CPAP). CPAP, as currently practiced, involves connection of a pressurized air delivering device to the mouth or nose of the patient. This device typically is connected to a pressurized air source in the form of a compressor or tank with a regulator. These pressurized air supplies are expensive, large, and noisy. Because body position and sleep stages vary throughout the night, the CPAP mask pressure often does not remain constant. To address this problem, many sleep clinicians select a sufficiently high pressure setting to ensure that respiratory disturbances are reliably inhibited even in the least favorable situations. Unfortunately, this necessitates a needlessly high mask pressure for periods during which it is not required. Furthermore, the high mask pressure may make CPAP uncomfortable. Variable patient compliance remains a significant problem. Studies have found that up to 25% of patients discontinue CPAP therapy.

Airway dryness may also contribute to CPAP discomfort. The high flow rates used during CPAP may overwhelm the capacity of the nasal mucosa to heat and humidity inspired air. Compounding this problem is a phenomenon known as mouth leak. Mouth leak occurs during approximately one-third of total sleep time in people who suffer from dryness of the nose and throat. It results from the mouth being partially or fully open during nasal CPAP therapy. During mouth leak, a portion of air bypasses the nasal membranes and exits via the mouth. Normally, expiratory air releases heat and water back into the nasal mucosa by condensing on the cooled mucosal surface. Leaked air is not conditioned in this way, and results in intensification of the excessive dryness experienced during the use of CPAP. To compensate for the decreased heat and humidification caused by moth leak, blood vessels in the nose dilate; however, their capacity to do so may be overwhelmed by the high flow rates produced by CPAP. As the patient continues to mouth leak, further moisture is lost and blood vessels continue to dilate, thereby narrowing the airway. The net result of this process is increased nasal resistance and nasal congestion.

It is known that such snoring can be alleviated by displacing the individual's lower jaw into a position that is relatively forward of its normal position. A variety of known devices are designed to forwardly displace an individual's lower jaw while they are sleeping to thereby alleviate snoring. Brace-like bite splints of this type for preventing snoring serve to move the mandibula slightly forwards, since in this position of the mandibula the respiratory tracts are opened wider, enabling a person to breathe more freely without snoring. Some appliances hold the lower jaw forward during sleep while others affect tongue position. Oral appliances relieve OSAS and snoring by realigning the jaw and/or tongue in relation to the head. Oral appliance therapy, while increasingly popular to treat selected cases of sleep disordered breathing, is not completely effective in all situations.

Oral appliances can be categorized generally into three types based on design. The first type mechanically lifts the soft palate. The effectiveness of this appliance type is presumed to be due to a prevention of collapse at the velopharyngeal level. The second type positions the tongue anteriorly while the mandible retains its customary relation to the maxilla. Some oral appliances of this type use a suction cup; others are designed to work through nocturnal neuromuscular training. Most oral appliances are of the third type-mandibular advancement appliances—which, as the name implies, advance the mandible. Because the mandible is the attachment for the genioglossus and other tongue muscles, the tongue moves anteriorly, as it does with the second type. The mechanism of action of the second and third of these oral appliance designs is to enlarge the hypopharyngeal airway by moving the base of the tongue farther from contact with the posterior wall of the pharynx, thereby reducing the likelihood of collapse from inspiration.

Nasal sprays mainly work as a snoring remedy for those who suffer from nasal blockage. Snoring caused by problems with the uvula or soft palate (as most snoring problems are) are not resolved by the use of, nasal sprays or nasal passage opening devices.

U.S. Pat. No. 5,465,734 to Snorex, Inc discloses a tongue retaining device formed of a flexible polyvinyl material and hollow interior that fits over the tongue and requires a specialist to take upper and lower jaw impressions of the patient to produce a tailored device for the patient.

Numerous attempts have been made towards treating OSA and snoring. These include placing implants in either the tissue of the soft palate or the pharyngeal airway as disclosed in U.S. Pat. No. 6,250,307 to Conrad et al. and U.S. Pat. No. 6,431,174 to Knudson et al. After implantation, tissue grows into the attachment ends and a bioresorbable member resorbs after tissue in-growth, causing tissue contraction, which results in a debulking of the tissue and movement of tissue away from opposing tissue surfaces in the pharyngeal upper airway.

Physicians often treat minor snoring by recommending that patients take simple measures such as increasing exercise, losing weight, decreasing alcohol consumption, reducing smoking, altering sleeping position, and using dental or nasal appliances. Although these relatively simple measures can be somewhat effective, many patients do not experience satisfactory relief from snoring. As a result, for many patients the only alternative is surgery.

One of the earliest surgical procedures developed, which is still in use today, is uvulopalatopharygoplasty. In addition to the poor success rates of this expensive procedure, various complications were common, including serious postoperative bleeding, pain, velopharyngeal incompetence, palatal dryness, nasopharyngeal stenosis, long-term voice changes and partial loss of taste.

Other palatal stiffening procedures, called radio frequency ablation (RFA), have been employed with mixed results, where radio frequency energy is delivered to the soft palate to cause scarring of the palatal muscle. Unfortunately, RFA must be performed multiple times to obtain satisfactory results.

In U.S. Pat. No. 5,988,171 to Sohn et al., suture material is placed around a base of the tongue and secured to the jaw, thereby moving the tissue of the base of the tongue away from the opposing tissue of the pharyngeal airway. This procedure, referred to as tongue suspension, is uncomfortable. Another technique described in U.S. Pat. No. 5,843,021 to Edwards et al., includes applying radio frequency ablation to either the tongue base or of the soft palate to debulk the tissue of the tongue or palate, respectively.

Other snoring remedies involve the injecting of a microparticle solution into a patient's soft palate to stiffen the soft palate, thereby stiffening the soft palate with the injected composition to reduce palatal flutter.

Unfortunately, all current treatments produce results that are far from optimal. Surgery and re-positioning devices are effective in only a minority of OSA patients and many people are subjected to painful and expensive procedures without benefit. While CPAP is effective in many situations, the treatment is uncomfortable and not well tolerated during long-term use. A substantial number of patients given CPAP discontinue therapy within the first year after initiation. Surgical procedures to remedy snoring are expensive, painful, and of dubious long-term benefit.

There is a long-felt but unsolved need for a simple, effective, inexpensive non-surgical method and device for treating snoring, especially one that does not rely upon uncomfortable mouth or tongue repositioners or the use of continuous positive airway pressure machines.

To date, nonsurgical approaches to the management of OSAS include behavioral modification, drug therapy, continuous positive airway pressure (CPAP), and use of mechanical devices. Behavioral modifications include avoidance of alcohol and sedative medications, alteration of sleep position, avoidance of sleep deprivation, and weight loss.

SUMMARY OF THE INVENTION

The present invention is directed to an improved method, system and product to provide desired palatal stiffening to achieve a reduction of snoring by reducing or substantially eliminating palatal flutter. In various embodiments, the present invention achieves desired stiffening of the soft palate to reduce palatal flutter through the use of mucosal strips that are positioned in a person's mouth before sleep. Unlike the prior art methods and devices that require permanent tissue changes, such as implantation of material, such as pillar system tubes, micro-particles, or the creation of scar tissue so as to affect the physical characteristics of the soft palate, the present invention is used only during times when snoring is an issue—e.g. mainly at night. Thus, during hours when a person is awake, there are no adverse tissue changes to the soft palate that would cause pain, affect breathing or talking or swallowing, which are issues that the prior art systems and methods present. Nor does the present method and system involve the embarrassing and uncomfortable use of jaw or tongue adjustment devices that are both uncomfortable and awkward in situations where a person is in bed with another person, such as a spouse who is also attempting to sleep. Instead, the use of the mucosal strip as set forth herein provides a relatively discrete way in which a person can avoid snoring by stiffening the soft palate tissue for a predetermined time period that is limited in duration, such that in many cases, the strip is dissolved by morning. Moreover, the person with a snoring problem can self adjust the amount of strips employed to address the vagrities of a particular person's soft palate area, need for stiffness, particular placement for comfort and effectiveness, etc. Unlike other devices that are a "one-size-fits-all" proposition, the ability to use more than one strip; to overlap strips, to reinsert strips during the night if snoring issues appear, etc. is made possible to adjust for particular situations and to address the severity of a particular person's snoring at any given particular moment.

Another aspect of the present invention includes the ability to load or impregnate the mucosal strips with any number of active agents to achieve other desirable aspects, such as breath freshening; administration of particular vitamins, medicinal components, salving of mouth sores, short or long term medication through buccal and mucosal tissues, etc.

The particular dimensions, thickness, size, area surface texture, flexibility, adhesive characteristics, flavoring and taste, composition (e.g. in terms of medicine, vitamins, nutraceuticals, etc.) for a particular strip can be adjusted as one of skill in the art will appreciate. In one embodiment, and unlike most presently available breath strips (e.g. such as Listerine breath strips) the strips employed in the present invention are both thicker, so as to provide more structural integrity to soft palate tissues upon which such strips adhere, and also have more long term (from at least about 5 minutes to several hours), preferably for at least about 3 hours, more preferably at least about 5 hours and most preferably at least about 6 or more hours—roughly equating to the period of time of a person's sleep and/or length of snoring experience. Moreover, in preferred embodiments the mucosal strips are designed to adhere well with each other when placed on palate tissue so that layering of the strips can be accomplished so as to custom build a desired thickness of the strips over tissue to be covered. This permits a user to layer as many strips as deemed necessary to stiffen the soft palate tissue in a manner that is personally comfortable for such user while also being sufficient to address the particular snoring issue experienced by such user. The area of tissue to be covered can be addressed by either having the person provide strips side-by-side to cover the area; by having certain tissue areas provided with thicker ultimate strip depth than other areas (e.g. providing for the option of stiffening certain palate soft tissue more than directly adjacent tissue), and even providing strips having different characteristics in terms of a variety of factors, such as taste, composition, adherence or dissolvability characteristics, area, shape, thickness, flavor, duration of flexibility characteristics, etc. In some embodiments, films of desired thickness and having desired properties in terms of dissolving rate, flexibility, provision of stiffness over time, adhesion duration, ability to cause reversible contraction of soft palate tissue (e.g. to thus enhance the desired stiffening of targeted tissue that would otherwise vibrate during snoring), can be fashioned, by cutting, forming in a particular mold, etc. to cover a desired soft palate area. For example, the particular physical area of an individual's soft palate will vary in size, dimensions, degree of soft tissue available for undesired vibration during a snoring episode, etc. and so cutting films, strips, areas of pre-manufactured material to cover such areas is made possible by the present invention. In other words, while in some embodiments standard sized strips of material may be available such that a person can layer, place side-by-side, orient distinctly, etc. strips of appropriately selected strips, on other embodiments, custom strips or films having particular shapes, such as one that covers the particular area of that particular person's soft palate tissue region, is contemplated. As disclosed herein below, strips are referred alternatively to oral films, mucosal films, etc.

Oral films having desired duration of adhesion and freedom from an adverse feeling in the oral cavity on use are selected that adhere to the particular regions of a person's soft palate, thereby stiffening the region and reducing or eliminating snoring.

Preferably, a hydrophilic pressure-adhesive hydrogel is employed that has desirable characteristics. In one embodiment, a hydrophobic pressure-sensitive adhesive or bioadhesives is used to provide desired control of tack, adhesive and water sorption properties required for optimal application mucosal tissue. U.S. Pat. No. 5,166,233 to Kuroya, et al. is incorporated herein by this reference for suitable adhesives in this regard. U.S. Pat. No. 6,552,024 to Choi is likewise incorporated herein in its entirety by this reference, as is U.S. Pat. No. 7,906,140 to Bromley, et al.; U.S. Pat. No. 6,803,420 to Cleary et al.; U.S. Pat. No. 7,984,714 to Hausmann et al.; U.S. Pat. No. 7,276,246 to Zhang; U.S. Pat. No. 5,578,315 to Chien et al.; U.S. Pat. No. 7,470,397 to Meathrel et al. U.S. Pat. Publication No. 20110033542 to Myers, et al.; U.S. Pat. No. 7,138,135 to Chen; U.S. Pat. No. 7,441,559 to Nelson.

Suitable oral films may be formulated using polymers, plasticizers, flavors, colors and sweeteners. The oral films are manufactured using solvent casting method, rolling method, extrusion method and solid dispersion method. Oral films are preferably selected that are not fast dissolving film and that will therefore remain in the oral cavity for a longer time and retained at the site of application. Oral film strips have hit the mainstream in the last few years as a new way of freshening the breath.

Polymers: The polymer may be water soluble, water insoluble, or a combination of one or more either water soluble or water insoluble polymers. The polymer may include cellulose or a cellulose derivative. Specific examples of useful water soluble polymers include, but are not limited to, pullulan, hydroxypropylmethyl cellulose, hydroxyethyl cellulose, hydroxypropyl cellulose, polyvinyl pyrrolidone, carboxymethyl cellulose, polyvinyl alcohol, sodium aginate, polyethylene glycol, xanthan gum, tragancanth gum, guar gum, acacia gum, arabic gum, polyacrylic acid, methylmethacrylate copolymer, carboxyvinyl copolymers, starch, and combinations thereof.

Plasticizers: Plasticizers include glycerin, sorbitol, propylene glycol, polyethylene glycol, triacetin, triethyl citrate (TEC), acetyl triethyl citrate (ATEC) and other citrate esters. plasticizer is added to improve flexibility of film.[5]

Flavoring agents: Flavoring agents, the essential oils or water soluble extracts of menthol, wintergreen, peppermint, sweet mint, spearmint, vanillin, cherry, chocolate, cinnamon, clove, lemon, orange etc.

Sweetening agents: Sweetening agent such as sugar, dextrose, lactose, mannitol, sucrose, xylitol, malitol, acesulfame potassium, talin, glycyrrhizin, sucralose, aspartame, saccharin etc.

Coloring agents: Coloring agents may include FD & C coloring agents, natural coloring agents, and natural juice concentrates, pigments such as titanium oxide, silicon dioxide and zinc oxide.

One (or a combination) of the following processes may be used to manufacture the oral films: solvent casting; Hot-melt extrusion; Solid dispersion extrusion; and Rolling.

Solvent Casting: The oral film is preferably formulated using the solvent-casting method, whereby the water-soluble ingredients are dissolved to form a clear viscous solution. Entrapped air is removed by vacuum. The resulting solution is cast as a film and allowed to dry, which is then cut into pieces of the desired size. Water-soluble hydrocolloids used to prepare films include: hydroxypropylmethyl cellulose (HPMC), hydroxypropyl cellulose (HPC), pullulan, sodium alginate, pectin and carboxymethyl cellulose (CMC).

Hot melt extrusion (HME) is used to prepare granules, sustained-release tablets, transdermal and transmucosal drug delivery systems. Processing films by this technique, involves shaping a polymer into a film via the heating process rather than through the traditional solvent casting method.

Solid dispersion extrusion: The term "solid dispersions" refers to the dispersion of one or more active ingredients in an inert carrier in a solid state in the presence of amorphous hydrophilic polymers and also using methods such as melt extrusion.

Rolling method involves preparation of a film by preparation of a pre-mix, addition of an active and subsequent formation of a film. For example, a master batch which includes the film-forming polymer, polar solvent, and any other additives is added to the master batch feed tank and is controllably fed via a first metering pump and control valve to either or both of the first and second mixers. After blending for a sufficient time to provide a uniform matrix, a specific amount of the uniform matrix is then fed to the pan through the second metering pumps. The metering roller determines the thickness of the film and applies it to the application roller. The film is finally formed on the substrate and carried away via the support roller. The wet film is then dried using controlled bottom drying, desirably in the absence of external air currents or heat on the top (exposed) surface of the film. A disintegration test may be employed to determine the time, at which a film breaks when brought into contact with water or saliva. The disintegration time is the time when a film starts to break or disintegrate. Thickness and mass play a role in determining the dissolvable film's physical properties. The "tensile strength" (psi) is the property of film that requires a load to cause load deformation failure of film. Tensile strength was evaluated according to ASTM International Test Method for Thin Plastic Sheeting (D 882-02). An electronic dynamometer AG/MC1 (Acquati, I) may be used and tensile strength and elongation may be calculated to arrive at a suitable strop for the intended uses and applications as set forth herein. Tensile strength (N/mm$^2$)=Breaking force (N)/Cross-sectional area of sample (mm$^2$) Percent elongation is measured when the film snaps as sufficient force applied so as to exceed the elastic limit. Elongation at break (%)=Increase in length at breaking point (mm)/Original length (mm)×100%. Thickness tests may be carried out using an electronic micrometer MI-1000 (Cheminstruments, USA). The thickness of the film sample may be measured using a micrometer (Digimatic Micrometer, Mitutoyo, Tokyo, Japan) at five locations (center and four corners), and the mean thickness calculated. Folding endurance is determined by repeatedly folding a small strip of film at the same place till it breaks. Film flexibility may be determined by adapting the ASTM bend mandrel test (D 4338-97) and a film may be bent over a mandrel and examined for cracks over the area of the bend in a strong light.

Taste masking for oral film systems can be employed so that any offensive bitter or poor taste of is addressed. One method of taste-masking is encapsulation by a polymeric covering sufficient to mask the taste of the film. Orally disintegrating thin films based on a water-soluble polymer are selected so that the film does not disintegrate rapidly within seconds after contact with water or saliva, but rather, is retained on the mucosal membrane for a significant period of time, preferably several hours, so that the film remains in place during the sleep of the person employing the same. Films prepared using chitin or chitosan are suitable as an oral mucoadhesive and water-resisting adhesive.

A suitable oral mucosa adhesive includes one that is at least moderately water-soluble, pliant polymer artificial dentifrice (AD) film that may be prepared from a hydroxypropyl cellulose-M (HPC-M) ethanol and polyethylene glycol. When applied to the wet surface of the mucosa, films of the present invention preferably show excellent adhesion and are able to cover oral mucosa long enough to last for a substantial period of time while the person is asleep. Such films provide mechanical stabilization of the tissue of the pharyngeal wall.

FIG. 1 shows, in cross-section, a naso-pharyngeal area of an untreated patient. FIG. 1 shows the nose N, mouth M and throat TH. The tongue T is shown in an oral cavity OC of the mouth. A hard palate HP (containing a bone B) separates the oral cavity OC from the nasal cavity NC. The nasal concha C (soft tissue which defines, in part, the nasal sinus—not shown) resides in the nasal cavity NC.

The soft palate SP (a muscle activated soft tissue not supported by bone) depends in cantilevered manner at a leading end LE from the hard palate HP and terminates at a trailing end TE. Below the soft palate SP, the pharyngeal wall PW defines the throat passage TP. A nasal passage NP connects the nasal cavity NC to the pharyngeal wall PW. Below an epiglottis EP, the throat passage TP divides into a trachea TR for passing air to the lungs and an esophagus ES for passing food and drink to the stomach.

The soft palate SP is operated by muscles (not separately shown and labeled) to lift the soft palate SP to urge the trailing edge TE against the rear area of the pharyngeal wall PW. This seals the nasal cavity NC from the oral cavity OC during swallowing. The epiglottis EP closes the trachea TR during swallowing and drinking and opens for breathing.

For purposes of this disclosure, the nasal cavity NC, oral cavity OC and throat passage TP are collectively referred to as the naso-pharyngeal area of the patient (defining, in part, the pharyngeal airway PA in FIGS. 5 and 13) with the area including the various body surfaces which cooperate to define the nasal cavity NC, oral cavity OC and throat passage TP. These body surfaces include outer surfaces of the nasal concha C, the upper and lower surfaces of the soft palate SP and outer surfaces of the pharyngeal wall PW. Outer surfaces means surfaces exposed to air. Both the upper and lower surfaces of the soft palate SP are outer surfaces. Snoring can result from vibration of any one of a number of surfaces or structures of the naso-pharyngeal area. Most commonly, snoring is attributable to vibration of the soft palate SP. However, vibratory action of the nasal concha C and the pharyngeal wall PW can also contribute to snoring sounds. It is not uncommon for vibratory action from more than one region of the naso-pharyngeal area to contribute to snoring sounds. Sleep apnea can result from partial or full collapse of the naso-pharyngeal wall during sleep.

Incorporated in its entirety by this reference is patent publication No. 20070218114 to Duggan. In various embodiments, the present invention includes a soluble composition for the administration of an active ingredient to a site on the mucus membranes of the throat of a human or animal subject.

In certain embodiments, a base material of a material having predetermined dissolving characteristics, formed as an inter-oral film (similar in various respect to available breath freshening strips) is selected to act as a stiffening substrate for a person's soft palate tissue. As the base material dissolves, under action of moisture in the mouth or on open skin or wound, the ability to retain desired tension of the underlying tissue is maintained for a period of time sufficient to reduce the incidence of snoring. In some embodiments, a controlled quantity of an active ingredient is released and is delivered to the soft tissue at the back of the throat it is able to have the desired effects. Such active ingredients may include those believed to also address snoring of an individual, and thus, the strips of the present invention also act (in addition to the structural support for damping or reducing undesired vibration of soft palate tissue) as delivery devices for such anti-snoring (or other medicinal purpose) materials, substances and compounds.

Reference herein to a strip is to any soluble prolonged release presentation of the composition which is conformable and is adapted to lie in a subject's mouth without causing obstruction or interfering with breathing, talking or swallowing or the like, or to conform to the surface of a subjects open skin or wound. Preferably the strip comprises a flexible film or the like. In use, the strip to be placed in a subject's mouth is intended to be placed at the back of the throat, near to the desired area of operation. Preferably the strip (or strips, whether layered, certain portions more dissolvable than others, etc.) are positioned on a person's soft palate. This can be achieved via a person's fingers or through the use of an applicator (otherwise described and illustrated.) The strip is particularly suited to delivery of ingredients having activity in relation to snoring or apnea, by delivery to the mucosa of the throat, in particular at the soft tissue in the pharyngeal region of the back of the throat, to keep the pharyngeal membranes moist and lubricated. The strip is conformed as a relatively thin planar structure to facilitate desired rates of inter-oral dissolution. For example, in certain embodiments, a single strip may be preferably no more than about 150 micron thick, more preferably in the range 100-400 micron thick, and in other embodiments may be over 500 microns in thickness. In other embodiments, however, the ability to layer strips on top of one another provides for the manufacture and availability of strips of more traditional thickness, such as those for example of the breath strips of Listerine, etc. The strip may be of any suitable shape, for example being square or rectangular for ease of storage, placement, distribution in packages, but is preferably generally planar and approximately 0.5 to 2 cm in length and breadth. Again, the particular shape and dimensions of a strip can be varied as required to address individual snoring issues, the degree of tissue stiffness of the soft palate required to address a particular snoring issue, etc. Thus one aspect of the present invention is that a person may modify the number, placement, kind, type, shape, time of application, frequency of application, etc. to address particular situations, which may vary over time and under any given set of circumstances. No prior art method or device employed in the battle against snoring offers such a variety and flexibility of treatment options as do the various embodiments of the present invention.

In certain embodiments, the strip is manufactured from a material which is soluble within the subject's mouth under the action of saliva and oral enzymes, o under the action of tissue fluids. In other embodiments, however, the strip is made so as not to dissolve and thus, is repeatedly applied to a person's soft palate at bedtime to alleviate snoring. A reusable device that adds the requisite structure to the particular soft palate tissue can have appropriate adhesive integral or added as needed to remain in a desired position. The customization of such a strip in terms of shape, size, characteristics regarding flavor, thickness, adhesive qualities etc. are within the present scope of the invention.

In certain embodiments, the base material for the strip is any suitable soluble solid material, which term includes gel-like and other materials which are sufficiently solid to enable the strip to be conformed to its desired shape. In particular, a carrier or base material of the strip may comprises a soluble gel material, and is for example based upon on an organic gel, which could for example be a fish, animal, bovine or marine gelatin or vegetal gelatin-like product, a polysaccharide, a cellulosic material, pectin such as from fruits, or other suitable base. Other materials may be added to the base gel, for example to stabilize, add other effects flavor etc. The carrier or soluble base material may be inert, or may itself have an activity or other desired property, whether in relation to the primary purpose of the invention or otherwise.

The no-snore strip of the present invention may further include one or more compositions, or alternatively, may solely be provided with materials meant and intended solely to provide desired structural support to reduce vibrational movement of soft palate tissues. Active agents may be used either impregnated in the strip material, added later (e.g. anti-snoring agents can be sprayed on such strips), layered in a fashion so that an adhesive strip is separate from an active layer strip; the provision of strips that can encompass or otherwise carry one or more active ingredient strips, liquids, etc. in a pouch (not shown) such that administration of various active ingredients can be achieved via attachment of an active ingredient container to the soft palate adhesive strip. Time release and slow release aspects of delivery can be achieved via suitable selection of permeable barriers employed to contain active ingredients and then the association of such barriers to soft palate adhesive strips. The layering of strip for separate and distinct purposes of structural tissue support versus for administering active ingredients is a entire segment of different embodiments of the present invention.

Components that can be included in strips or associated with strips in the various ways described herein include agents that may include additional active ingredients, including a plurality of active ingredients having an activity in relation to a particular condition or the throat or throat disorder, oral conditions, or conditions of snoring and/or sleep apnoea, open skin or wound healing or repair agents and/or active ingredients having other desired activity.

Preferably in certain embodiments, active ingredients include at least one active ingredient with physical (moisturizing, lubricating, cooling etc) or pharmacological (for example decongestant, anti-histamine, anti-bacterial, anti-inflammatory, analgesic etc) activity. For example active ingredients might include ingredients having any desired physical or pharmacological activity on the mucous membranes of the throat, including without limitation decongestants, lubricants, antibacterial and antiseptic compositions, anti-histamines, anti-inflammatory compositions, analgesics, and other medicaments and non-medicaments. Additional ingredients may include breath-fresheners and deodorizers. Inactive ingredients may be added in suspension or solution for example to stabilize or preserve the soluble base, balance the pH of the base, bring the base to closer approximation to isotonic concentration etc. The composition may additionally include adjuvants and the like such as vitamins for example selected from Ascorbic acid (vitamin C) which enhance the active ingredient effect. The composition may include additional ingredients for formulation purposes, for example selected from sodium chloride which maintains favorable isotonicity.

In still other embodiments, the use of additional ingredients may provide for chemical binding, and for example for the use of liposome technology, can be employed. In some embodiments of the invention a part or all of the active ingredients are encapsulated within encapsulation structures selected to provide the desired degree of adhesion to the mucous membranes of the throat, and adapted to release the active ingredients slowly over time in situ. These encapsulation structures may be distributed within the base material in the strip composition. In one embodiment, the encapsulation structures comprise multilamellar microparticles. The multilamellar microparticles are selected to exhibit good adhesion to the mucous membranes of the throat, and are small enough to be effectively distributed in the strip. The multiple layers may be structured to give slow release of the active ingredient over the desired time period, so that a single strip dose gives sustained activity over time, for example providing for measurable activity for a sustained period of four or more hours, and ideally of for example 6 to 12 hours, to give overnight effectiveness.

Microparticles are preferably sized and shaped to form an effective distribution within the base material in the strip as a composition in accordance with the invention. The microparticles in particular comprise generally spherical particles or microspheres. Particle sizes in the range 0.1 to 50 .mu.m, and for example 1 to 20 .mu.m are likely to be preferred. Particle levels of 5-25% within the composition are preferred but depend on the particular tissue characteristics being addressed. For example, tissue stiffening materials can be employed that dissolve at different rates and that affect the amount and number of strips that may be required to address snoring issues over time. Microparticles may be are adapted to facilitate slow release of the active ingredients over time, and are preferably inherently able to show good adhesion to the mucous membranes of the throat. Active ingredients are thus stabilized in situ on the mucous membranes at the back of the throat, and then released steadily at the site where they are required.

Using the present invention, it becomes possible to maintain reasonable levels of activity over the sort of time scale necessary to be effective overnight, and for example to assist in providing a relatively less disturbed night's sleep. Microparticles comprise multiple layered structures formulated with one or more of: surfactant layers (comprising any type of surfactant such as anionic, non-anionic, cationic, phospholipids and the like such as sucroesters and guar hydroxypropyltrimonium chloride), and hydrophobic or lipophilic materials such as aliphatic and aromatic hydrocarbons, optionally halogenated, higher alcohols, ketones and the like, for example including Vitamins (A, E, D), carotenoides, polyphenols, vegetable oils, essential oils, phytosterols, lipophilic preservatives, menthol, linalool, eucalyptol, and the like; and polar layers including solvents or polar media such as water, glycerol, PEG, sorbitol, glycol, hydrophilic materials such as alcohols or ethoxylated alcohols, carboxylic acids or salt of a fatty acid, quaternary ammonium derivatives, sulphonates or sulphates and the like, vitamins (B, C), flavonoides, 18-beta glycyrrhetinic acid and derivatives, glycerol, active ingredients such as plant extract as hereinbefore defined; hydrophilic preservative; cellulose polymer, hyaluronic acid and derivatives, alpha-hydroxide acid, and the like. Also possible inclusion are pectin; cellulose; sodium hyaluronate; guar hydroxypropyltrimonium chloride; polysorbate 60, and optionally additionally cellulose; xanthan gum; chitosan or quaternary ammonium. In one embodiment, such strip composition comprises: solvent 30-60%, Humectant 8-14%, Texturant 0-2%, Preservative 0-2%, and a Acidity regulator 0-1% (all by weight). Microparticles thus preferably comprise multilamellar structures of surfactant layers, which are able to encapsulate active ingredients to a very high degree for protection and controlled release—whether that be rapid release (e.g. for certain tissue stiffening components) or longer term release, such as breath freshing components). The strips are formulated to be adapted to enhance adhesion to human skin, and hence to fix the particles in position on the mucous membranes of the throat. Suitable compositions include 30 to 50% surfactant, 30 to 50% polar medium, and 10 to 60% active binding agent, comprising hydrophilic and hydrophobic agents as appropriate.

Microparticles providing the controlled binding for slow release of physically active ingredients at the active site on the mucous membrane of the throat of the human, non-human mammal or other animal subject to provide an active effect, bind effectively to the membranes to stiffen the tissue and thus reduce or eliminate undesired snoring. Microparticles are advantageous to fix the active ingredients adsorbed within each shaped layer in position on the mucous membranes of the user, protect the active ingredients and slowly release them in situ, and might also assist in providing a desired lubricating effect. Active or inactive ingredients might be provided either encapsulated within the microparticles or separately in suspension or solution within the base for various purposes.

Formulation of oral drug strips involves the application of both aesthetic and performance characteristics such as strip-forming polymers, plasticizers, active pharmaceutical ingredient, sweetening agents, saliva stimulating agent, flavoring agents, coloring agents, stabilizing and thickening agents. From the regulatory perspectives, all excipients used in the formulation of oral drug strips should be approved for use in oral pharmaceutical dosage forms. For example, films that incorporate a pharmaceutically active ingredient are disclosed in expired U.S. Pat. No. 4,136,145 to Fuchs, et al. These films may be formed into a sheet, dried and then cut into individual doses. The Fuchs disclosure alleges the fabrication of a uniform film, which includes the combination of water-soluble polymers, surfactants, flavors, sweeteners, plasticizers and drugs. These allegedly flexible films are disclosed as being useful for oral, topical or enteral use. Examples of specific uses disclosed by Fuchs include application of the films to mucosal membrane areas of the body, including the mouth, rectal, vaginal, nasal and ear areas.

With respect to manufacturing of strips, one of skill in the art will appreciate the various methods and components involved to achieve desired qualitative and quantitative aspects. For example, if a dissolvable strip is intended to last over a several hour period, the changes in content of materials used in the manufacture, for example, of breath strips, can be adjusted to lengthen the time it takes to dissolve such strip. Flavor, binding and adhesion abilities, etc. are adjusted suitably to achieve desired results. Thus, while the present specification provides some detail as to how to make and use certain embodiments of the present invention, reliance on incorporation by reference is appropriate to encompass the myriad of ways in which a particular product is produced. All of such techniques, however, are well within the skill of one of ordinary skill in the art in view of the guidance and direction provided herein.

Thin films are typically made using wet casting manufacturing process and may be, for example, up to a maximum of 10 mils thick, as above such thickness it being commonly understood that matrix like products become "sheets" when they exceed a thickness of 10 mils. Wet cast film manufacture and products are described in U.S. Pat. Nos. 7,425,292 and 5,948,430, also incorporated herein in its entirety by this reference. Films may initially have a thickness of about 500 .mu.m to about 1,500 .mu.m, or about 20 mils to about 60 mils, and when dried have a thickness from about 3 .mu.m to about 250 .mu.m, or about 0.1 mils to about 10 mils. Desirably, the dried films will have a thickness of about 2 mils to about 8 mils, and more desirably, from about 3 mils to about 6 mils. The thickness of films may exceed 2.7 mils despite some adverse mouth feel.

Thickness can relate to dissolution time especially if certain formulae are used. Wet cast monolayer film compositions for pharmaceutical and vitamin delivery are disclosed in Fuchs et al. U.S. Pat. No. 4,136,162. Schmidt discloses bilayer film compositions for pharmaceutical and food uses in U.S. Pat. No. 4,849,246. and Leung U.S. Pat. No. 6,923,981, Fuisz et al. US 20080075825, 20090098192 to Fuisz, Slominski et al US 20060207721, Fankhauser et al, US 2007/0202057, Laskey U.S. Pat. No. 1,492,600, Repka et al U.S. Pat. No. 6,375,963, Schiraldi, U.S. Pat. No. 6,072,100, Yang et al. U.S. Pat. Nos. 7,357,891 and 7,425,292, and Pharmaceutical Extrusion Technology, edited by Issac Ghebre-Sellassie and Charles Martin (2007) also incorporated in their entireties by this reference.

Preferably the strips of the present invention are made in a manner that do not dissolve in fewer than ten seconds, thus distinguishing the same from common breath strips widely available. The strops of the present invention may have a weight of from 30 to several hundred mg., preferably over 33 mg. Preferably, strops of the present invention have sufficiently high moisture content to impart the product with flexibility and to avoid becoming brittle, e.g. the strips should preferably avoid cracking when bent.

In certain embodiments, the methods employed by Mono-Sol Rx with respect to a thin film drug delivery technology can be used, preferably providing a strop having a relatively thin film, which is similar in size, shape and thickness to a postage stamp. Preferably, the strips of the present invention, when containing active ingredients, have the ability to carry doses of prescription products up to 80 mg or exceeding 1000 mg, and even more preferably, over 200 mg. Suitable taste masking agents can be employed depending upon the active ingredients involved.

Other embodiments of the present invention are directed to multiple film laminates that can have distinct adherence and qualitative features and components associated with separate layers, thus facilitating differences in manufacture, activity, structural characteristics, such a s flexibility, dissolution rate, etc. The strips of the present invention provide the requisite pliability and tensile strength necessary to securely adhere to a person's mucosal tissues for at least one hour, more preferably at least two hours, and even preferably a bioadhesive polymer is selected from the group consisting of polycarbophil, carbomer, one or more acrylic polymers, one or more polyacrylic acids, copolymers of these polymers, a water soluble salt of a copolymer of methyl vinyl ether and maleic acid or anhydride, a combination thereof and their salts.

In other embodiments, to achieve the desired thickness of strips for structural support purposes of the present invention, a so-called slab or sheet manufacturing technique is employed that uses a nonaqueous, extrudable composition comprising at least one thermoplastic polymer in an amount of more than 20 wt % of the whole composition, such composition comprising at least one thermoplastic polymer and one or more bioactive ingredients in a form that may be placed on the mucosa and having an average dissolution time of preferably more than 50 minutes, more preferably at least about 2 hours, and even more preferably at least about 5 hours. In some embodiments the strip is in a sheet and has a surface area of approximately 0.25-1.5 in. and a thickness of approximately 10-70 mil.

A strip may be impregnated or coated with a dose of active ingredient and other components. Strips may be coated with other components as desired. Suitably strips are made up in bulk films which are subsequently cut to size and shape as hereinbefore defined.

For purposes of written description and enablement of the various embodiments of the present invention, the following published applications and issued patents are incorporated herein by this reference in their entireties: U.S. Pat. Nos. 7,067,116 and 7,648,712 to Bess, et al.; U.S. Pat. No. 7,632,525 to Dodds, et al.; U.S. Pat. No. 6,502,574 to Stevens, et al.; 20050159637 to Nelson et al.; U.S. Pat. No. 7,845,356 to Paraschac et al.; U.S. Pat. No. 7,824,588 to Yang et al.; 20090098192 to Fuisz; U.S. Pat. No. 7,500,484 to Nelson; Fentanyl compound-containing edible patch to be applied to oral mucosa, to Furusawa et al.; U.S. Pat. No. 7,566,310 to Badr et al.; U.S. Pat. No. 5,190,053 to Meer et al.; Schmidt U.S. Pat. Nos. 6,748,951 and 6,467,485.

In still other embodiments, to avoid fears that adhesion will not suffice to attach a trop to a person's soft palate tissue, strips can also be afforded an attachment line, such as dental floss, so that the strip can be also anchored to one's teeth, tooth or around the tongue to ensure that the strip does not present a choking hazard if dethatched. Thus in one embodiment, a loop or segment of dental floss anchored to teeth or around gum line or a tongue can prevent swallowing of the strip if it become detached.

Preferably, strips of the present invention comprise a mixture of at least three types of film forming agents, such as maltodextrins, fillers (for example, microcrystalline cellulose (MCC)) and hydrocolloids (for example, sodium aliginate), suitably adapted to adhere to oral surfaces of an oral cavity, and in particular the soft palate. While structural support for the soft palate is the principal direction of the present invention, as this reduces or eliminates snoring, other embodiments also comprise the use of such strips to deliver or release oral care agent(s). Such agents include anti-microbial agents and salivary stimulants to treat, for example, halitosis, dental plaque, gingivitis, xerostomia, dry mouth, like oral conditions or combinations thereof. Further, the oral care edible film can act as a breath freshener effective against malodor. In other embodiments, both a longer acting (if not entirely non-dissolvable strip) can be employed in association with one or more other strips having other desired characteristics. For example, a structural support strip can be used to reduce snoring while an additional strip can be associated with such structural strip to achieve breath freshening, delivery of a medicinal compound, etc.—with such second strip having entirely distinct dissolution characteristics.

The oral cleansing and breath freshening effects of the edible film of the present invention can be achieved by entrapping the oral care agents within the oral cavity to provide extended efficacy. In this regard, the highly dissolvable edible film can act as a medium through which a pharmaceutically active oral agent can be administered via a mucous membrane of the oral cavity.

Strips may further include a variety of other suitable ingredients, such as softeners, colorants, flavoring agents, emulsifiers, surface active agents, thickening agents, binding agents, sweeteners, fragrances, other like ingredients or combinations thereof.

The strips may comprise a hydrocolloid of any suitable type, amount and number of hydrocolloids. In an embodiment, the hydrocolloid can constitute between about 10% to about 50% by dry weight of the edible film, preferably about 20% to about 30% by dry weight. The hydrocolloid can be derived from, for example, natural seaweeds, natural seed gum, natural plant exudates, natural fiber extracts, biosynthetic gums, gelatins, biosynthetic process starch or cellulosic materials, alginates, sodium alginate, calcium alginate, carrageenans, guar gum, locust gum, tara gum, gum arabic, ghatti gum, agar gum, xanthan gum, pectin, other like hydrocolloid source material or combinations thereof.

The present invention also relates to a method for placing the anti-snore strip on the soft palate, as by an applicator having a handle and an extension that attaches reversibly to a strip and that can be positioned to deliver the strip to the soft palate without causing a gag reflex from the user.

In certain embodiments of the present invention, the size and number of adhesive strips contacting the soft palate of a person can be varied. For example, while a larger size strip (e.g. an expanse of material that covers a particular area of soft palate tissue) can be greater than the dimensional area of a person's soft palate, thereby extending beyond the perimeter of the soft palate, it can also be of a smaller area and may extend therefore over only some—e.g. a central portion; half of the area of the soft palate—leaving the other side of the soft palate area uncovered by any strip, etc. Moreover, more than one strip can be employed to attach to the soft palate region, such as by providing two separate smaller strips on the soft palate with some space between, more preferably at least three or more individual strips within the soft palate region. The general objective of placing one or more strips in or about the soft palate region is intended to provide required structural support for the tissue in a manner that reduces the instances of vibration of such tissues in a way that results in snoring. So in certain embodiments, strips of various desired shapes and sizes can be employed to populate the area of one's soft palate to dampen vibrational movement caused by the passage of air through the region when asleep. In some individuals, the surface area of adhesive strips will be relatively minor as compared to others, who may require substantially all of the soft palate tissue area to be covered to achieve the objective of reduced snoring. Due to the possible discomfort caused by any adhesive strip being positioned for a lengthy period of time on one's throat, the goal would be to present a minimum area of strip that also accomplishes the desired reduction or elimination of snoring. Moreover, with the slight risk that a larger strip may become detached and cause undesired blockage of air flow, possible chocking, etc. there is a desire to reduce the amount of material being positioned in one's throat to address snoring problems. By administering the minimum number of strips, using strips of the smallest dimensions in terms of thickness, projection from the tissue into the airflow path, etc. such concerns are addressed. Thus, in one embodiment, the application of dots of adhesive strip material may be sufficient to address snoring issues, with such dots being of such a small size that both airflow restriction and chocking concerns are not significant. The use of such smaller sized strips also eliminate the need for some type of anchoring device or member, such as may be useful when larger strips are employed. In such larger area strip uses, dental floss-type anchors can be secured to the strip (where dental floss loops or extensions can be securely connected with or integral with such strips) and the other end of such dental floss can be secured to some other feature to prevent unintended swallowing or inhalation of the strip if the strip were to become loose from the soft palate tissue. Layering or over-lapping of smaller strips may also be useful to address such airflow and/or choking concerns while still addressing the overall objective of reducing vibrations of the tissue, e.g. stiffening the soft palate in a fashion that reduces the occurrence of snoring.

In still other embodiments, other structural members can be associated with the adhesive strips.

In still other embodiments of the invention, wafer-type structures can be employed to address the stiffening of soft palate tissue. These wafers, preferably having one side sticky so that it adheres well for a predetermined amount of time to a person's mucosal membrane, but with the other side not sticky, and more preferably lubricated (e.g. thorough the use of lubricants that are imbedded in the strips, such as via microencapsulated lubricants, etc.) to facilitate both comfort to the user, avoidance of undesired adherence of soft palate to other tissues, etc.

Incorporated herein by this reference is 20110009834 to Asmussen with respect to various particular components that can be utilized to form strips. The strip-shaped forms can comprise a flexible material suitable for pharmaceutical and/or cosmetic use by humans and/or in animals, i.e. materials that do not have any unwanted side effects. Unwanted side effects would be toxic effects, the causing of irritations or the triggering of allergic reactions, for example. Suitable materials may be, for example, thermoplastic polymers, thermoset polymers, copolymer films, paper, waxes, textiles (nonwovens, knitted fabrics and woven fabrics), chalks, films, gels and wood composites, as well as combinations of the aforementioned materials. Specific polymers suitable as material for the strips may be selected from the group of polymers consisting of cellulose ethers, methyl acrylates, hydroxyalkyl celluloses such as hydroxypropyl methyl cellulose, hydroxypropyl cellulose, hydroxyethyl cellulose, methyl cellulose and carboxymethyl cellulose, polysulfones, polyvinyl pyrrolidones, crosslinked polyvinyl pyrrolidones, polyvinyl pyrrolidone-vinyl acetate copolymers, polyvinyl alcohols, polyacrylic acids, polyacrylate polymers, crosslinked polyacrylic acids, polyethylene oxides, polyethylene glycols, polyvinyl alkyl ether-maleic acid imide copolymers and carboxyvinyl polymers. Suitable polymers may also be selected from the group of polymers consisting of marine colloids, natural gums and polysaccharides. These polymers include, for example, sodium alginate, carrageenan, xanthan gum, gum acacia, gum arabic, guar gum, pullulan, agar, chitin, chitosan, pectin, karaya gum, zein, hordein, gliadin, carob meal, tragacanth and other polysaccharides, starches such as maltodextrins, amylose, amylopectin, maize starch, potato starch, rice starch, tapioca starch, pea starch, sweet potato starch, barley starch, wheat starch, waxy maize starch, modified starch, dextrins, levan, elsinan and gluten; and proteins such as collagen, whey protein, casein, milk protein, soya protein, gelatine, waxes and colophony, as well as synthetic waxes and bees wax. By combining two or more of the aforementioned polymers, the properties of the strip of material, such as mucoadhesiveness, flexibility, solubility behaviour, swelling behaviour and the like, can be adapted according to one's wishes and requirements. The strip of material, or the layers of the strip of material, comprise/comprises at least one polymer, which represents an essential component of the strip of material or of the layer(s). The polymer portion amounts to at least 5%-wt. and preferably not more than 90%-wt., preferably 10 to 70%-wt., more preferably 30 to 60%-wt., in each case relative to the strip of material or the layer, respectively. The strip of material, or individual layers of the strip of material, can furthermore contain excipients or additives in order to control the chemical or physical properties, such as flexibility, mucoadhesive properties, disintegratability, swellability and/or diffusion properties. To be taken into consideration as excipients or additives are, in particular, substances selected from the group consisting of antioxidants, emulsifiers, gelling agents, flavour enhancers, taste corrigents, flavours, sweeteners, stabilisers, pH regulators, acidifying agents, bulking agents, preservatives, colourings, thickening agents, plasticisers and humectants. Those skilled in the art will know suitable excipients and additives approved for pharmaceutical applications.

In one embodiment, the strip has a surface adapted to promote tissue in-growth. The tissue in-growth promoting surface is desirably selected from a group of outer surfaces including a textured surface, a porous surface, a braided surface, a mesh surface, a fleece surface, and a coating for inducing bone or tissue in-growth.

One aspect of the present invention is directed to re-shaping the soft palate in a manner that reduces snoring. Use of the strips of the present invention can achieve such a feat by building up the structural integrity of the soft palate in a fashion so that, after time and proper treatment regimens, the shape of the soft palate is reformed to open up the airway and reduce snoring noise. Thus the present invention may be used to re-shape the soft palate for minimizing the likelihood of obstructive sleep apnea episodes associated with long, flat soft palates and/or L-shaped soft palates. In one embodiment, when a long, flat soft palate is causing OSA, an implant having a curved body may be implanted into the soft palate for increasing the curve of the soft palate. In another embodiment, when an L-shaped soft palate is causing OSA, an implant may be inserted for reducing the curve or angle of the soft palate. Thus, in one embodiment, a plurality of implants having varying radii may be provided, whereby an implant having a desired amount of curve may be utilized for increasing or reducing the curve of the soft palate (i.e changing the shape of the soft palate). In one embodiment, a plurality of implants having varying sizes may be provided so as to enable medical personnel to select an implant having a desired size. In addition to affecting the soft palate, the strips of the present invention may further be used in supporting the uvula in a manner that provides more positive positioning of the uvula and enables the uvula to provide greater resistance to distal tongue movement, thus providing a balanced level of uvula support which provides tongue support when needed, but does not inhibit swallowing. The shape changing feature of the strips allows greater uvula support (and thereby tongue support) during times of rest, and less support during waking hours.

In one embodiment, the strips can comprise collagen or other tissue growth enhancing material to further the stiffening of the soft palate so as to reduce the occurrence of vibration when a person is sleeping. Collagen allows for the tissue in growth (tissue engineering). The collagen can be in many types and forms, or in combinations thereof. For example, collagen can be Type I, II or III. Collagen can be native, denatured or cross linked. The various types and forms of collagen are described generally in Methods in Enzymol. (1982) 82:3-217, Pt. A, the contents of which is herein incorporated reference. For example, collagen can be produced from animal derived tissues such as bovine hides, human tissues such as cadaver skin or human cell cultures or through recombinant methods.

In still other embodiments, the strips are positioned to overlap with the hard palate as well as the soft palate, thereby modifying the airflow of a person to reduce snoring. In such embodiments, only a portion of the soft palate is covered by such a strip as it may not be necessary to have the entire soft palate encompassed to achieve desired snoring reduction.

In other embodiments, the strips may be used to plump up the soft palate tissue in a manner that makes such tissue more stiff or rigid to a degree that snoring is reduced due to the reduction in vibrations of such tissue once plumped. Use of various active agents in contact with and/or administered via the strips can achieve this plumping of the soft palate tissue. Slight irritation of the tissue may achieve the similarly desired stiffening of the tissue and thus, slightly irritating agents can likewise be utilized. Thus, in a teaching away from prior art references, use of slightly "toxic" substances may actually be beneficial to achieve the sought after reduction in tissue vibration of the soft palate. Such "toxic" substances may also or in addition be simply toxic to bacteria and other foreign agents.

The strip surfaces themselves can be modified to achieve desired airflow characteristics. Thus, channels can be provided to guide airflow in a manner that reduces snoring noise. The surface of the strip can be similar to a foam layer such that an insulation layer is provided that adds support for tissue while also dampening undesired sound or vibrations during sleep. The height, temperature and construction of layers on a strip can be adjusted for particular problems encountered in the wide variety of personal snoring issues. The flexibility of the strip as a whole or in portions thereof can be modified to address comfort and support issues. Thus, certain portions of the strip may be more solid to dampen vibrations, while other portions may be more flexible to accommodate comfort concerns of a user.

The present invention provides a non-surgical procedure to alleviate snoring and thus, is devoid of the pain, incisions, pre- and post operative requirements and complications, etc. of surgical procedures used to address snoring problems. The strips are applied in a temporary rather than permanent manner and thus avoid the complications one may have when micro-beads are implanted into tissue that may cause infections, adverse reactions, etc. Nor is the present invention one where mandible adjustment is required, although it can be used in association or in parallel with such other non-surgical devices to assist in achieving a reduction of snoring. The present invention envisions treatment for snoring only during the sleeping hours of an individual without having any appliance that would interfere with the cosmetic nature of one's appearance in bed. For example, a sexual partner in bed may find it objectionable to a person having to apply a mandibular adjustment device that may interfere with kissing, romantic encounters, etc. Obviously, air flow machines would similarly interfere with such intimate moments. In contrast, the present invention may enhance such occasions as no outward appliance would be viewable or encountered by a sexual partner. Moreover, with possible breath freshening components added to the strip, morning breath and bad breath issues would be addressed, while the reduction in snoring would itself lead to a happier bedtime experience for both the wearer and his/her partner.

A buccal bioadhesive strip, especially one having no active drugs, when applied to the soft palate, stiffens the tissue to reduce vibration, and thus snoring sounds, of an individual. The strips preferably have a surface that is anti-microbial in nature, such that such strips assist in reducing the surface area in the mouth where noxious odors may arise due to the proliferation of foul smelling agents produced by bacteria that can survive in one's mouth.

Thus, one aspect of the present invention is directed to the novel combination of a specifically surface structured bioadhesively attachable, and in a preferred embodiment, dissolvable, strip of material that persists in the mouth for at least one hour and preferably at least about 3 hours, so as to stiffen the tissue of the throat, specifically the soft palate, and thus reduce the occurrence of snoring. The ability to defeat the proliferation of bacteria in a person's mouth can significantly decrease the occurrence of so-called "morning breath".

In one embodiment, a buccal bioadhesive strip having no active drugs, that when applied to the soft palate, stiffens the tissue to reduce vibration, and thus snoring sounds, of an individual. The strips preferably have a surface that is anti-microbial in nature, such that such strips assist in reducing the surface area in the mouth where noxious odors may arise due to the proliferation of foul smelling agents produced by bacteria that can survive in one's mouth.

Thus, one aspect of the present invention is directed to the novel combination of a specifically surface structured bioadhesively attachable and dissolvable strip of material that persists in the mouth for at least one hour and preferably at least about 3 hours, so as to stiffen the tissue of the throat, specifically the soft palate, and thus reduce the occurrence of snoring. The ability to defeat the proliferation of bacteria in a person's mouth can significantly decrease the occurrence of so-called "morning breath".

In various embodiments, the disclosure of various patent publications owned by Sharklet TM (mentioned herein) are incorporated herein by this reference. Thus, in certain embodiments, a mucosal adhesive strip has a coated surface for resisting bioadhesion (or in other aspects, enhancing bioadhesion—so as to further the stiffening characteristics of the anti-snoring strip) that includes at least one patterned polymer including coating layer having a plurality of features attached to or projected into a base surface. The features each have at least one microscale (<1 mm) dimension and have at least one neighboring feature having a substantially different geometry. The patterned coating layer preferably provides an average roughness factor (R) of from 4 to 50. The coating layer resists or enhances bioadhesion as compared to the base surface. An article having a surface coating with topography for controlling bioadhesion comprises a base surface, at least one patterned polymer comprising coating layer including a plurality of spaced apart features attached to or projected into the base surface which provide at least a first feature spacing distance. The features each have at least one microscale dimension and at least one neighboring feature having a substantially different geometry. The coating layer provides an average roughness factor (R) of from 2 to 50, preferably being from 4 to 50. The coating layer resists or enhances bioadhesion as compared to the base surface Other aspects of the present invention are directed to a method of preparing an edible water-soluble film composition, said method comprising: a) preparing a master batch of film-forming components comprising a water-soluble polymer, a foam reducing flavoring agent selected from the group consisting of menthol, cherry menthol, cinnamon, spearmint, peppermint, orange flavor, natural raspberry, and combinations thereof, and a polar solvent, wherein said foam reducing flavoring agent is added before mixing said polymer with said solvent; b) mixing said film-forming components under vacuum; c) wet casting said film-forming components; and d) removing said polar solvent through a controlled drying process to form said edible water-soluble film; wherein said film is free of added defoaming agents. Historically films and the process of making drug delivery systems therefrom have suffered from a number of unfavorable characteristics that have not allowed them to be used in practice. Films that incorporate a pharmaceutically active ingredient are disclosed in expired U.S. Pat. No. 4,136,145 to Fuchs, et al. ("Fuchs"). These films may be formed into a sheet, dried and then cut into individual doses. The Fuchs disclosure alleges the fabrication of a uniform film, which includes the combination of water soluble polymers, surfactants, flavors, sweeteners, plastickers and drugs. These allegedly flexible films are disclosed as being useful for oral, topical or enteral use. Examples of specific uses disclosed by Fuchs include application of the films to mucosal membrane areas of the body, including the mouth, rectal, vaginal, nasal and ear areas.

The formation of agglomerates randomly distributes the film components and any active present as well. In certain embodiments, certain portions of the film or strips employed are purposefully not uniform with respect to the dispersion and location of active ingredients. Thus, contrary to many prior art teachings, the provision of a uniform film is not particularly desired in several embodiments. In fact, films having better adhesive characteristics around the edges, e.g. where the hard palate is contacted, and less in the soft palate contacting region of the strip, are preferred for different embodiments. Like the differences in concentration and presence of active ingredients in any particular portion of a strip, so too are the physical characteristics of a strip not necessarily uniform in various embodiments. Thus, the flexibility and stiffness of certain regions of a strip may be adjusted to comport with desired objectives, such as avoidance of tissue irritation, the provision of adhesive to the strips, inclusion of different drugs, active agents, etc in various amounts, types and positions in the strip, including different time release agents that are released at different times during the strip's contact with a mucosal membrane. The problems of self-aggregation leading to non-uniformity of a film were addressed in U.S. Pat. No. 4,849,246 to Schmidt, incorporated herein by this reference. Schmidt specifically pointed out that the methods disclosed by Fuchs did not provide a uniform film and recognized that that the creation of a non-uniform film necessarily prevents accurate dosing, which as discussed above is especially important in the pharmaceutical area. Other U.S. Patents directly addressed the problems of particle self-aggregation and non-uniformity inherent in conventional film forming techniques. U.S. Pat. No. 5,629,003 to Horstmann et al. and U.S. Pat. No. 5,948,430 to Zerbe et al. incorporated herein by this reference, relate to additional ingredients, i.e. gel formers and polyhydric alcohols respectively, to increase the viscosity of the film prior to drying in an effort to reduce aggregation of the components in the film.

Conventional drying methods generally include the use of forced hot air using a drying oven, drying tunnel, and the like. Such methods can be usefully employed in various embodiments of the present invention, and thus, in a teaching away from the prior art, such methods can be cost effectively employed to achieve desired strips having predetermined characteristics that do not relate to uniformity of dose, thickness, etc. This makes it far easier to manufacture devices for use and reduces the costs to the ultimate consumer. Because the films are often very thin, it can be a challenge to incorporate a high load of active ingredient while maintaining the film's uniformity. In various embodiments, this is not a concern, as it is for prior art inventions, as uniformity is not that imperative to achieve mere structural support for otherwise vibrating tissue of one's throat.

Another factor affecting the uniformity of films is the prevention of air bubbles in the film. Anti-foaming and/or defoaming components may be used to aid in the removal of air, such as entrapped air, from the film-forming compositions. Such entrapped air may lead to non-uniform films. These can be used in certain embodiments of the invention, but primarily to facilitate other objectives, such as reduction in waste, etc. One example of a conventional anti-foaming/defoaming component is simethicone. Simethicone reduces the surface tension of bubbles air located in the solution, such as foam bubbles, causing their collapse. An alcohol/water mixture is known to lower water density as well as lower the water's surface tension. So, any air bubbles trapped inside this mixture solution will also be dissipated. Simethicone acts as an anti-foaming/defoaming component by both lowering the surface energy of any air bubbles trapped inside the aqueous solution, as well as lowering the surface tension of the aqueous solution. Preferably, a foam reducing flavoring agent is employed that is present in amount of about 0.1% to about 20% by weight of the film. In another preferred embodiment, the foam reducing flavoring agent is present in amount of about 0.5% to about 15% by weight of the film and has a flavoring agent selected from the group consisting of menthol cherry menthol, cinnamon, spearmint, peppermint, orange flavor, natural raspberry and combinations thereof. In another preferred embodiment, the water-soluble polymer includes a polymer selected from the group consisting of a cellulosic material, polyethylene oxide, a polysaccharide, a gum, a protein, a starch, a glucan, and combinations thereof. In another embodiment, the water-soluble polymer is selected from the group consisting of carboxymethyl cellulose, hydroxyl methyl cellulose, hydroxyethyl cellulose, hydroxypropyl cellulose hydroxypropylmethyl cellulose, polyethylene oxide, and combinations thereof. In another embodiment, the water-soluble polymer is selected from the group consisting of gum arabic, xanthan gum, tragacanth, acacia, carageenan, guar gum, locust bean gum, pectin, alginates and combinations thereof. In another embodiment, the water-soluble polymer is selected from the group consisting of polydextrose, dextrin, dextran and combinations thereof.

The film can also include an active component. In one embodiment, the active component is selected from the group consisting of cosmetic agents, pharmaceutical agents, bioactive agents and combinations thereof. In another embodiment, the active component is present in amounts of up to about 60% by weight of the film.

The film can further include one or more agents selected from the group consisting of taste-masking agents, plasticizing agents, surfactants, emulsifying agents, thickening agents, binding agents, cooling agents, saliva-stimulating agents, sweetening agents, antimicrobial agents and combinations thereof.

In another aspect of the invention, a method of preparing an adhesive strip is provided. The method includes: a) preparing a film-forming composition comprising a water-soluble polymer, a foam reducing flavoring agent, and a polar solvent; b) mixing said film-forming composition under vacuum; c) casting said film-forming composition; and d) removing said polar solvent through a controlled drying process. Either a foam reducing flavoring agent or a conventional foam reducing agent can be used, the later preferred as the cost is less and the avoidance of active ingredients in a structural strip of the present invention does not necessitate such steps of the prior art.

Bioadhesion, in particular mucoadhesion, has been of interest for the development of controlled drug delivery systems to improve buccal and oral administration of drugs. The oral and nasal cavities, for example, form convenient and easily accessible sites for drug delivery. Carboxylated polymers, such as poly(acrylic acid) and crosslinked poly (acrylic acid), are known to be effective as mucoadhesives (hereinafter bioadhesive compositions). Various bioadhesive compositions comprising poly(acrylic acid) are described, e.g., in WO 98/22097; EP 410,696; U.S. Pat. No. 5,643,603; U.S. Pat. No. 4,915,948; U.S. Pat. No. 5,895,804 and U.S. Pat. No. 6,284,235, all of which are incorporated herein by this reference for particular embodiments of the invention.

The use of bioadhesive compositions comprising carboxylated polymers has, however, been limited owing to problems associated with mucosal irritation. While attempts to reduce the degree of irritation have included blending these polymers with other materials, including polysaccharides, efforts to produce non-irritating bioadhesive matrices have resulted in compositions having decreased bioadhesion, which limits the amount of drug that can be incorporated into the composition. In certain embodiments of the present invention, however, because of the limited time periods where mucosal contact is encountered, the use of such previously discouraged bioadhesives is suitable for the present invention. This direction away from what the prior art teaches is part of the novel characteristics of the present invention. Having said this, in certain embodiments, use of a bioadhesive composition having increased bioadhesive properties, decreased irritation, and, in certain embodiments, the capacity for higher drug loading, is desirable.

The term "bioadhesive delivery device" as used herein and in the appended claims means any solid substance, of any shape, which is intended to be adhered to a mucosal tissue of a subject. The term "buccal device" or "buccal delivery device" means a bioadhesive device which is intended to be inserted into the buccal cavity. The term "vaginal device" or "vaginal delivery device" means a bioadhesive device which is intended to be inserted into the vagina. All inventions are combinations of old elements. Only God works from nothing. Man must work with what already is. The task here, as it has always been, is to invent real tears, hard love, slow-spoken, ancient words, difficult as a child's first steps across a room.

The term "bioadhesive, closed-cell foam film, sustained release, delivery device" as used herein and in the appended claims means a bioadhesive delivery device comprising a closed-cell foam film substance designed to provide a sustained, controlled release an active agent or combination of active agents to a subject. These bioadhesive delivery devices preferably include buccal delivery devices and vaginal delivery devices.

The term "controlled release" as used herein and in the appended claims means that a predetermined dosage of an active agent or combination of active agents is administered to a subject over a period of time.

The term "bioadhesive force" as used herein and in the appended claims is a quantitative value for tackiness (grams) which simulates the adhesion of the bioadhesive, closed-cell foam film, sustained release, delivery devices of the present invention upon contact with a moist mucosal tissue. The bioadhesive force preferably should be at least 10 grams, more preferably at least 15 grams, most preferably at least 20 grams.

The term "tensile strength" as used herein and in the appended claims is expressed in pounds per square inch (psi) and is the property of a bioadhesive, closed-cell foam film, sustained release, delivery device of the present invention that requires a load to cause load deformation failure of said film.

The term "thickness" as used herein and in the appended claims by measurements in mil (a mil=one thousandth of an inch) is determined when a bioadhesive, closed-cell foam film, sustained release, delivery device of the present invention is placed between two microscopic slides.

The term "water content" as used herein and in the appended claims is the % residual water content per unit dose as measured to the Karl Fisher method and expressed as percent of the dry weight of a bioadhesive, closed-cell foam film, sustained release, delivery device of the present invention. Strips that may be used to provide desired characteristics can be obtained, for example, from: Monosol Rx, LLC (Portage, Ind.); or Lavipharm Laboratories Inc. (East Windsor, N.J.); and ARx.

In certain embodiments, a mucosal adhesive strip has a coated surface for resisting bioadhesion (or in other aspects, enhancing bioadhesion—so as to further the stiffening characteristics of the anti-snoring strip), such strips including at least one patterned polymer including coating layer having a plurality of features attached to or projected into a base surface. The features each have at least one microscale (<1 mm) dimension and have at least one neighboring feature having a substantially different geometry. The patterned coating layer preferably provides an average roughness factor (R) of from 4 to 50. Preferred embodiments include at least one coating layer that either resists or—alternatively—enhances bioadhesion as compared to the base surface. Thus, in one embodiment, a buccal bioadhesive strip has no active drugs and when applied to the soft palate, stiffens the tissue to reduce vibration, while its surface topography is effective in resisting bioadhesion. Such a strip comprises at least one coating layer that comprises a polymer, the coating layer having a pattern defined by a plurality of spaced apart features attached to or projected into a base surface, said plurality of features each having at least one microscale dimension and having at least one neighboring feature having a substantially different geometry, wherein an average spacing between adjacent ones of said features is between 0.5 and 5 .mu.m in at least a portion of the coating layer, the coating layer resisting bioadhesion as compared to said base surface. U.S. Pat. No. 7,143,709 is incorporated herein by this reference.

A strip of the present invention in various embodiments comprises a surface having a topography for controlling bioadhesion comprises a base surface, at least one patterned polymer comprising coating layer including a plurality of spaced apart features attached to or projected into the base surface which provide at least a first feature spacing distance. In certain embodiments, such topography has features that each have at least one microscale dimension and at least one neighboring feature having a substantially different geometry. Preferably, the strips have a surface layer imported to them that provides an average roughness factor (R) of from 2 to 50, preferably being from 4 to 50, and most preferably has an R factor of about 30.

In various embodiments, the present invention is distinguished from the prior art in one of several ways, including:
certain embodiments entail the use of a specially textured surface, either one both or at least the outer side of an adhesive strip (the side facing away from the mucosal tissue to which it is attached) that has anti-microbial characteristics. In one such embodiment, the surface topography is such that it resists bioadhesion of undesired bacteria that are typically present in a human's mouth. Such a surface may comprise a layer or coating that comprises a pattern defined by a plurality of spaced apart features attached to or projected into a base surface, with a plurality of features each having at least one microscale dimension and having at least one neighboring feature having a substantially different geometry, and having an average spacing between adjacent ones of said features of between 0.5 and 5 .mu.m. Incorporated herein by this reference is U.S. Pat. No. 7,650,848 to address written description and enablement issues regarding the use of suitable textures and surfaces that may be employed. Thus, preferred embodiments include strips that have a surface upon which bacteria do not like to grow, in particular, surfaces having a surface texture and/or pattern that faces away from the mucosal contacting side of the strip and that reduces the number of bacteria that would normally occupy such surface area of the mucosal membrane where the patch/strip no adhered thereto. creates a surface upon which bacteria do not like to grow. Exemplary surfaces that can be employed for such purpose include those in FIGS. 2(a-d)

Certain embodiments of the patch have overall geometries particularly suited for the individual's mouth and are customizable therefore. As such, perforated tear lines such that smaller sizes can be fashioned easily. Other geometries of strips are such that they limit common "gag reflexes" of a person, while still achieving the objective of reducing the vibrational flutter of tissue that causes snoring. Particular strips are designed so as to also extend over not only a majority of the soft palate region, but also over the hard palate, so as to father reduce the incidence of gag reflexes being triggered;
certain embodiments have toxic substances associated with the surface of the strips, thereby killing certain undesired bacteria in the mouth;
certain embodiments comprise bioluminescent strips to facilitate a user's ability to view (in a mirror) the correct placement of the strips in one's throat. Bioluminescence is a type of chemiluminescence and in certain embodiments, a catalytic protein increases the efficiency of chemiluminescent reaction such that a bioluminescent protein is determined by detecting the presence of luminescence. Bioluminescent compounds that may be employed in the present invention embodiments include luciferin, luciferase and aequorin. Other embodiments employ differences in visual appearance to determine whether a patch is placed properly; whether certain desired or undesired bacteria are present in the mouth, etc, and such effective means for determining the same include a film, coating or patch that includes one or more of the following characteristics: reflectance, retroreflectance, fluorescence, photoluminescent light transmission, color, tinting strength, and whiteness. In one particular embodiment, in addition to addressing snoring issues, certain embodiments may also assist in the detection of whether a person has a certain medical condition, such as strep throat. Thus, in one embodiment, the patch changes color, expresses bioluminescence, etc. if there is strep bacteria present in a predetermined amount. Incorporated herein by this reference for written description purposes is U. S. Pat. Publication No. 20110250626 to Williams, et al.
certain embodiments employ a non-fast drying adhesive to eliminate the discomfort sometimes associated with fast drying adhesives;
certain embodiments are devoid of paper, rice or hemp products;
certain embodiments have compounds residing thereon to facilitate the growth of desired bacteria, such as those deemed beneficial or at least not detrimental to a person's health, and in some circumstances, that build up in a manner that further promotes the reduction of vibration of the underlying tissue;
certain embodiments include the use of phase change materials such that when certain temperatures are encountered while in use, the phase change occurs, thus resulting in physical characteristics of the overall strip to be modified so as to, for example, increase the stiffness of the strip, reducing vibration of the underlying tissue, etc. Incorporated herein by this reference for the purpose of understanding the various characteristics and selection of appropriate phase change materials are the following: U.S. Pat. Nos. 7,666,502; and 7,579,078.
certain embodiments employ materials that cause the strip to stiffen when exposed to either vibration (such as that encountered during the snoring of an individual) or upon slight changes in temperature, such as caused by a person mouth snoring. In such a manner, when the strip experiences air flow that cools the materials, such as phase change material, it causes a stiffening of the strip, thus reducing the vibration of the underlying tissue to which the strip is adhered to;

certain embodiments include the provision of structural features that direct airflow in a manner that further reduces the occasion of throats tissue vibration. As such, for example, particular grooves, hollow structures and curved surfaces can be employed to address the particular air-flow patterns within a person's throat so as to reduce the occurrence of snoring. In one embodiment, heat reactive materials are included in the strip to effect a desired change or modification of stiffness of the strip under certain environmental conditions. For example, the strip is provided with a sufficient amount of heat change materials that when exposed to the increased air cooling effects caused by a person's snoring, act to stiffen the strip so as to add to the anti-virbrational characteristics of the strip when in contact with the soft palate of the individual snoring. When the passage of air over the soft palate is such that the temperature of the environment around the strip is warmer, the heat change materials react in a manner that lessens the rigidity of the overall strip. Various materials can be employed in various embodiments of the invention to achieve such desired results. For example, a suitable polymorph, such as polycaprolactone, a biodegradable polyester with a low melting point of around 60° C. (140° F.), can be used as one of several agents to achieve a desired flexibility of a strip.

Similarly, Shape Memory Polymers (SMP) can be re-shaped when exposed to heat and will retain this new shape after cooling down. SMPs can retain two or sometimes three shapes, and the transition between those is induced by temperature. In addition to temperature change, the shape change of SMPs can also be triggered by an electric or magnetic field, light or solution. As well as polymers in general, SMPs also cover a wide property-range from stable to biodegradable, from soft to hard, and from elastic to rigid, depending on the structural units that constitute the SMP. SMPs include thermoplastic and thermoset (covalently cross-linked) polymeric materials.

Heat-Shrink materials can also be used, such as those manufactured from a thermoplastic (such as nylon or polyolefin) which shrinks when exposed to heat. In certain embodiments, the material used contains many monomers that when heated, polymerise, increasing the density of the material as the monomers become bonded together and the volume of the material shrinks. Conversely, other heat shrink materials are expansion-based, where heating to just above the polymer's crystalline melting point permits the material to become less rigid and later cooling acts to relax. A mixture of such materials can be done to achieve desired overall characteristics of any particular strip for use for the present invention purposes.

Suitable environmentally changeable strips can, in addition to reliance on heat variance to modify physical rigidity characteristics, also have their rigidity modified via the degree of moisture absorbed by the strip. For example, when snoring, the air drying aspects of the throat causes the strip to lose moisture, and thus, increase in rigidity, thus causing a consequential stiffening of the underlying tissue to which the strip is adhesively attached. When snoring ceases, the air flow is reduced, lessening the moisture loss from the strip, and causing the strip to regain flexibility and become less rigid. Preferably, the materials used have a curing temperature suitable for body heat transitions experienced during a snoring episode, and thus heat-curable polymer particles have a curing temperature of about 96 degrees F. Incorporated herein by this reference is U.S. Pat. Pub. No. 20060188813 to Shimada for various materials that can be employed for the same, albeit modified to attain the desired temperature curing abilities for the purposes set forth herein. Edible prolamine and other edible coatings are preferred as they are non-toxic because they are formed from a naturally-occurring, common food protein, and can thus be used as they do not contain organic solvents or require extreme pH's.

DETAILED DESCRIPTION OF THE INVENTION

Snoring is attributable to vibration of the soft palate SP. Vibratory action of the nasal concha C and the pharyngeal wall PW can also contribute to snoring sounds. It is not uncommon for vibratory action from more than one region of the naso-pharyngeal area to contribute to snoring sounds. Sleep apnea can result from partial or full collapse of the naso-pharyngeal wall during sleep. The present invention provides a non-surgical procedure to alleviate snoring and thus, is devoid of the pain, incisions, pre- and post operative requirements and complications, etc. of surgical procedures used to address snoring problems. The strips are applied in a temporary rather than permanent manner and thus avoid the complications one may have when micro-beads are implanted into tissue that may cause infections, adverse reactions, etc. No prior art method or device employed in the battle againk snoring offers such a variety and flexibility of treatment options as do the various embodiments of the present invention.

Figure 1:
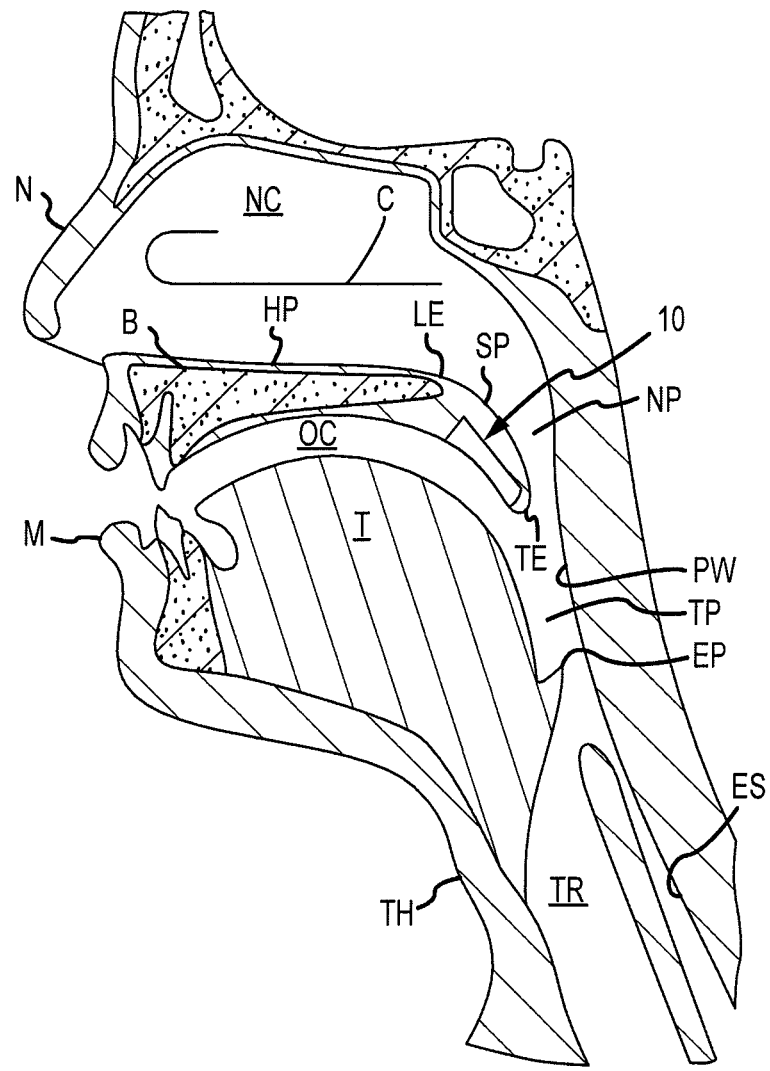
FIG. 1 is a cross-sectional view of a person's airway where a particular placement of a snore strip is shown associated with the soft palate.

FIG. 1 shows, in cross-section, a naso-pharyngeal area of an untreated patient. FIG. 1 shows the nose N, mouth M and throat TH. The tongue T is shown in an oral cavity OC of the mouth. A hard palate HP (containing a bone B) separates the oral cavity OC from the nasal cavity NC. The nasal concha C (soft tissue which defines, in part, the nasal sinus—not shown) resides in the nasal cavity NC.

The soft palate SP (a muscle activated soft tissue not supported by bone) depends in cantilevered manner at a leading end LE from the hard palate HP and terminates at a trailing end TE. Below the soft palate SP, the pharyngeal wall PW defines the throat passage TP. A nasal passage NP connects the nasal cavity NC to the pharyngeal wall PW. Below an epiglottis EP, the throat passage TP divides into a trachea TR for passing air to the lungs and an esophagus ES for passing food and drink to the stomach.

The soft palate SP is operated by muscles (not separately shown and labeled) to lift the soft palate SP to urge the trailing edge TE against the rear area of the pharyngeal wall PW. This seals the nasal cavity NC from the oral cavity OC during swallowing. The epiglottis EP closes the trachea TR during swallowing and drinking and opens for breathing.

For purposes of this disclosure, the nasal cavity NC, oral cavity OC and throat passage TP are collectively referred to as the naso-pharyngeal area of the patient with the area including the various body surfaces which cooperate to define the nasal cavity NC, oral cavity OC and throat passage TP. These body surfaces include outer surfaces of the nasal concha C, the upper and lower surfaces of the soft palate SP and outer surfaces of the pharyngeal wall PW. Outer surfaces means surfaces exposed to air. Both the upper and lower surfaces of the soft palate SP are outer surfaces.

Figure 2A:
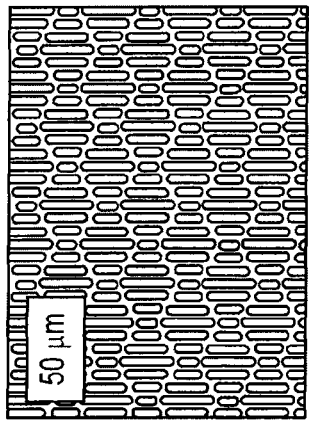
FIGS. 2(a)-(d) illustrate some exemplary surface architectural patterns according to the invention.
Figure 2B:
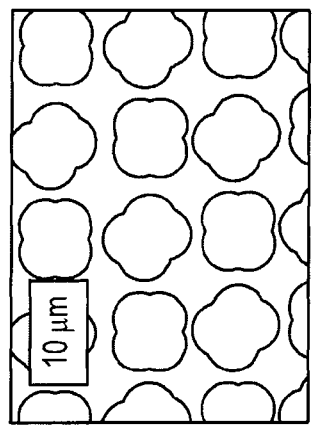
Figure 2C:
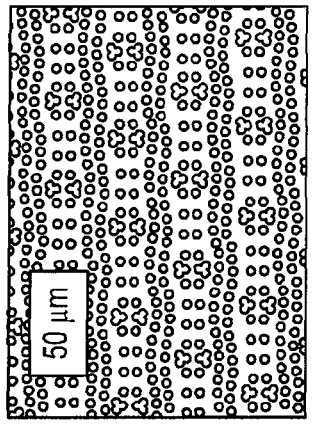
Figure 2D:
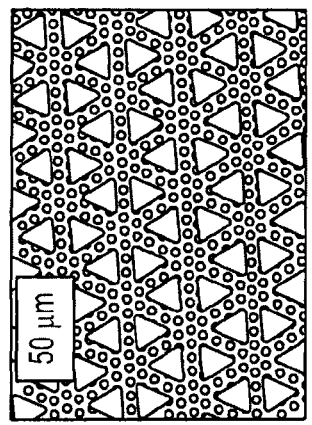

FIGS. 2(a)-(d) illustrate some exemplary architectural patterns that can be used with the invention. FIG. 2(a) shows a riblet pattern having features spaced about 2 µm apart; FIG. 2(b) shows a star/clover pattern, FIG. 2(c) a gradient pattern, while FIG. 2(d) shows a triangle/circle pattern.

Figure 3:
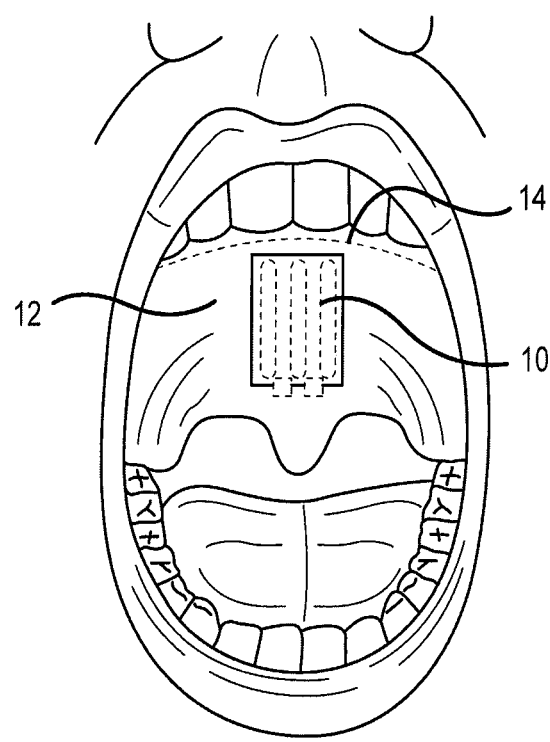
FIG. 3 is a front perspective view of a person's open mouth, illustrating the placement of a snore strip on the surface of the soft palate.

FIG. 3 is a front perspective view of a person's open mouth, illustrating the placement of a snore strip 10 on the surface of the soft palate 12, and the hard palate/soft palate junction 14. The area of tissue to be covered can be addressed by either having the person provide strips 10 side-by-side to cover the area; by having certain tissue areas provided with thicker ultimate strip depth than other areas (e.g. providing for the option of stiffening certain palate soft tissue 12 more than directly adjacent tissue), and even providing strips 10 having different characteristics in terms of a variety of factors, such as taste, composition, adherence or dissolvability characteristics, area, shape, thickness, flavor, duration of flexibility characteristics, etc. Films may be selected of desired thickness and having desired properties in terms of dissolving rate, flexibility, provision of stiffness over time, adhesion duration, ability to cause reversible contraction of soft palate tissue 12 (e.g. to thus enhance the desired stiffening of targeted tissue that would otherwise vibrate during snoring), and can be fashioned, by cutting, forming in a particular mold, etc. to cover a desired soft palate 12 area. Custom strips or films having particular shapes, such as one that covers the particular area of that particular person's soft palate 12 tissue region, is contemplated.

Figure 4A:
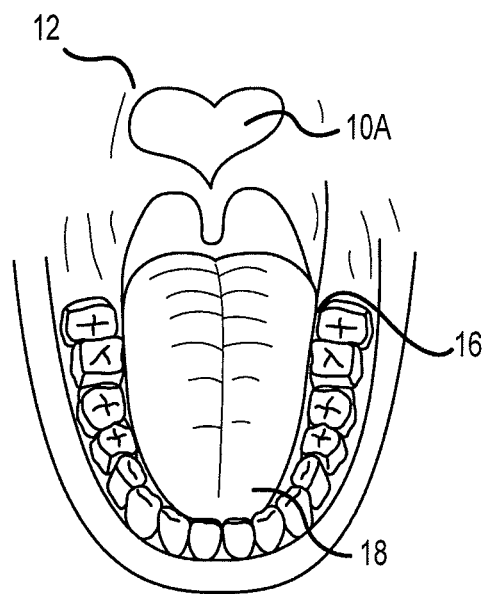
FIG. 4A is an illustration of a person's mouth with a heart-shaped snore strip associated with the soft palate and a teeth anchor associated with such snore strip.

FIG. 4A is an illustration of a person's mouth and tongue 18 with a heart-shaped snore strip 10A associated with the soft palate 12 and a teeth anchor 16 associated with such heart-shaped snore strip 10A.

Figure 4B:
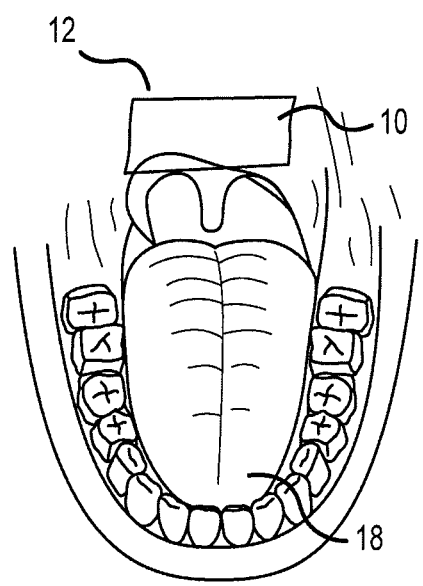
FIG. 4B is an illustration of a person's mouth with a rectangular shaped snore strip adhered to the soft palate with mucosal adhesive agents.

FIG. 4B is an illustration of a person's mouth and tongue 18 with a rectangular shaped snore strip 10 adhered to the soft palate 12 with mucosal adhesive agents. The strip 10 may be of any suitable shape, for example being square or rectangular for ease of storage, placement, distribution in packages, but is preferably generally planar and approximately 0.5 to 2 cm in length and breadth. Again, the particular shape and dimensions of a strip 10 can be varied as required to address individual snoring issues, the degree of tissue stiffness of the soft palate 12 required to address a particular snoring issue, etc. Thus one aspect of the present invention is that a person may modify the number, placement, kind, type, shape, time of application, frequency of application, etc. to address particular situations, which may vary over time and under any given set of circumstances. The customization of such a strip 10 in terms of shape, size, characteristics regarding flavor, thickness, adhesive qualities etc. are within the present scope of the invention.

Figure 5:
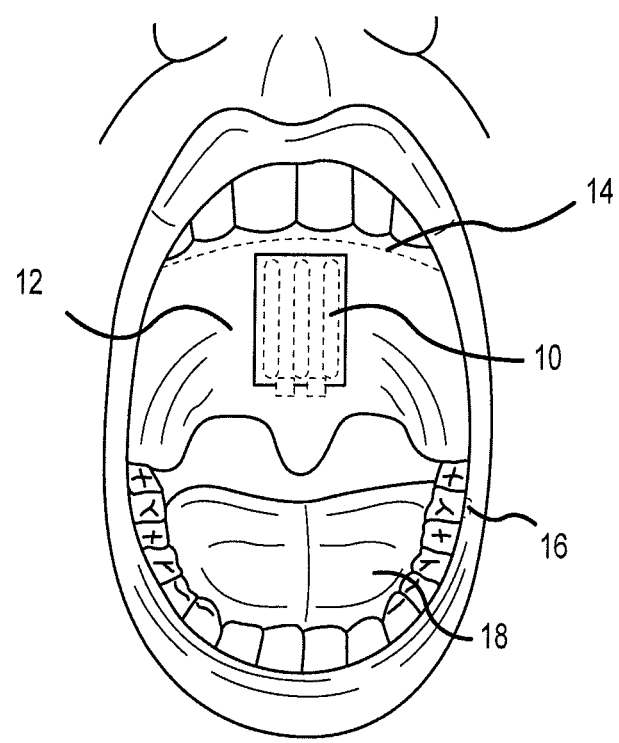
FIG. 5 is an illustration of a person's open mouth with a snore strip place on the soft palate and a dental floss attachment anchor associated between the strip and a the teeth.

FIG. 5 is an illustration of a person's open mouth and tongue 18 with a snore strip 10 placed on the soft palate 12 and an attachment anchor 16 associated between the strip 10 and the teeth. To avoid fears that adhesion will not suffice to attach a strip 10 to a person's soft palate 12 tissue, strips 10 can also be afforded an attachment anchor 16, such as dental floss, so that the strip 10 can be also anchored to one's teeth, tooth or around the tongue 18 to ensure that the strip 10 does not present a choking hazard if detached. Thus, in one embodiment, a loop or segment of dental floss anchored 16 to teeth or around gum line or a tongue can prevent swallowing of the strip 10 if it become detached.

Figure 6A:
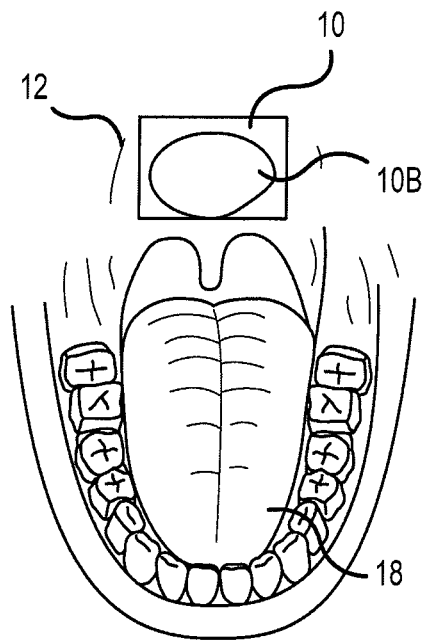
FIG. 6A is an illustration of a person's open mouth where a first rectangular snore strip is over-laid by a 2nd circular snore strip.

FIG. 6A is an illustration of a person's open mouth and tongue 18 where a first rectangular snore strip 10 is over-laid by a 2nd circular snore strip 10B. In one embodiment, the strips 10 employed provide more structural integrity to soft palate 12 tissues upon which such strips 10, 1 OB adhere, and also have long term function (from at least about 5 minutes to several hours), preferably for at least about 3 hours, more preferably at least about 5 hours and most preferably at least about 6 or more hours—roughly equating to the period of time of a person's sleep and/or length of snoring experience. The mucosal strips 10 are designed to adhere well with each other when placed on palate tissue 12 so that layering of the strips can be accomplished so as to custom build a desired thickness of the strips 10 over tissue 12 to be covered. This permits a user to layer as many strips as deemed necessary to stiffen the soft palate tissue 12 in a manner that is personally comfortable for such user while also being sufficient to address the particular snoring issue experienced by such user.

Figure 6B:
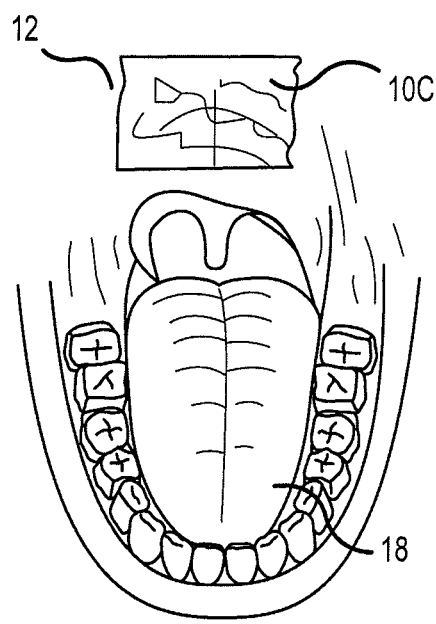
FIG. 6B illustrates a snore strip having structural support elements associated therewith.

FIG. 6B illustrates a snore strip 10 positioned above a person's tongue 18 having structural support elements 10C associated therewith. The no-snore strip 10 of the present invention may further include one or more compositions, or alternatively, may solely be provided with materials meant and intended solely to provide desired structural support to reduce vibrational movement of soft palate 12 tissues. Active agents may be used either impregnated in the strip 10 material, added later (e.g. anti-snoring agents can be sprayed on such strips), layered in a fashion so that an adhesive strip 10 is separate from an active layer strip 10; the provision of strips 10 that can encompass or otherwise carry one or more active ingredient strips 10, liquids, etc. in a pouch (not shown) such that administration of various active ingredients can be achieved via attachment of an active ingredient container to the soft palate 12 adhesive strip 10. Time release and slow release aspects of delivery can be achieved via suitable selection of permeable barriers employed to contain active ingredients and then the association of such barriers to soft palate 12 adhesive strips 10.

Figure 7:
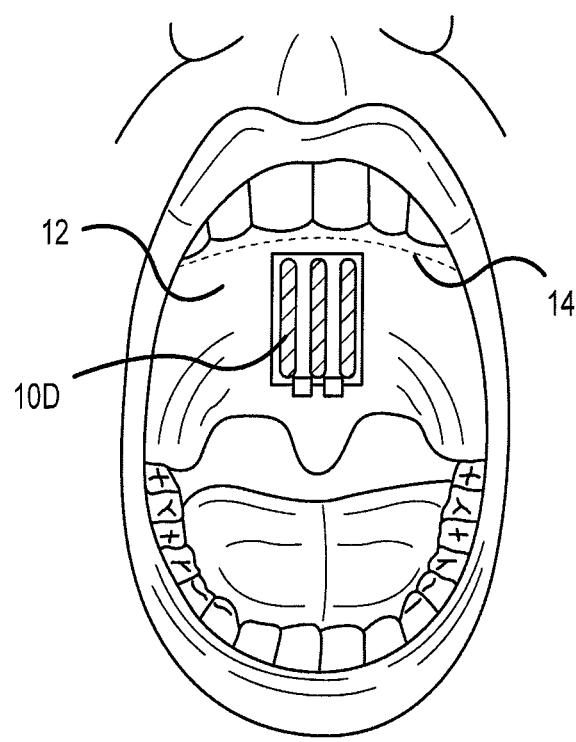
FIG. 7 illustrates a snore strip having a cross-hatched support structure integral with the strip to provide desired damping of vibrational movement of the soft palate.

FIG. 7 illustrates a snore strip 10 having a cross-hatched support structure 10D integral with the strip 10 to provide desired damping of vibrational movement of the soft palate 12. In one embodiment, the strips 10 can comprise collagen or other tissue growth enhancing material to further the stiffening of the soft palate 12 so as to reduce the occurrence of vibration when a person is sleeping. In still other embodiments, the strips 10 are positioned to overlap with the hard palate junction 14 as well as the soft palate 12, thereby modifying the airflow of a person to reduce snoring.

Figure 8:
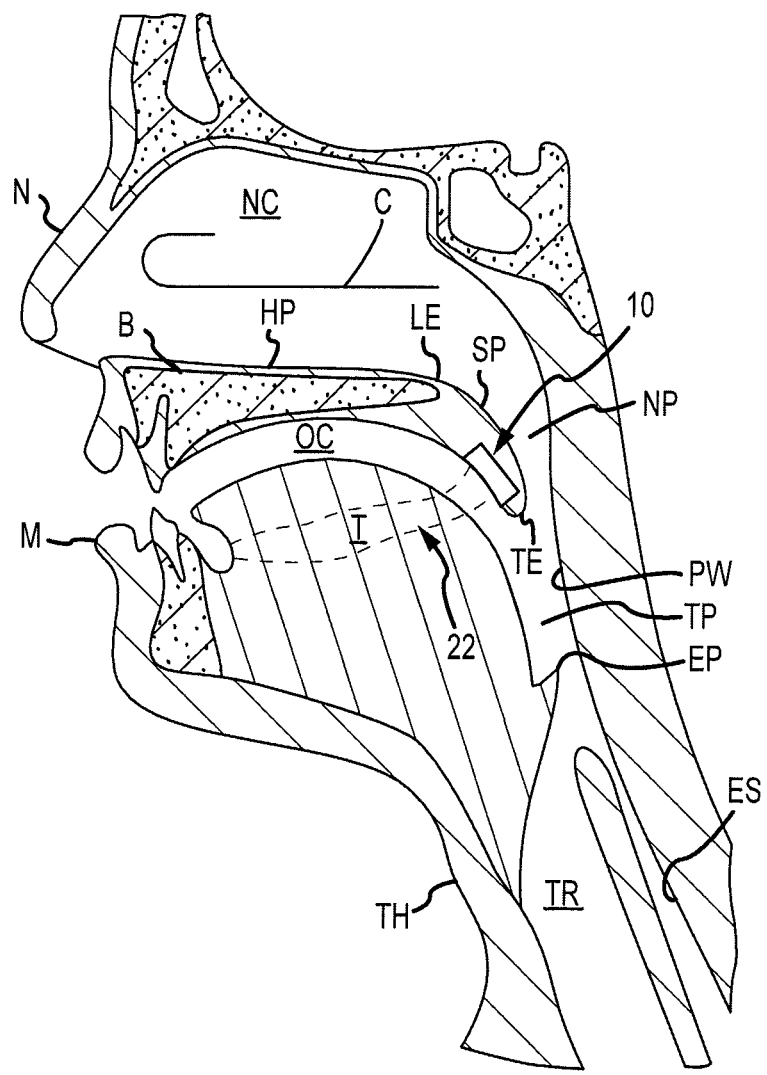
FIG. 8 is a cross-sectional view of a person's head where a snore strip is anchored by a tongue loop anchor.

FIG. 8 is a cross-sectional view of a person's head where a snore strip 10 is anchored by a tongue loop anchor 22. The general objective of placing one or more strips 10 in or about the soft palate 12 region is intended to provide required structural support for the tissue in a manner that reduces the instances of vibration of such tissues in a way that results in snoring. So in certain embodiments, strips 10 of various desired shapes and sizes can be employed to populate the area of one's soft palate 12 to dampen vibrational movement caused by the passage of air through the region when asleep. In some individuals, the surface area of adhesive strips 10 will be relatively minor as compared to others, who may require substantially all of the soft palate 12 tissue area to be covered to achieve the objective of reduced snoring.

Figure 9:
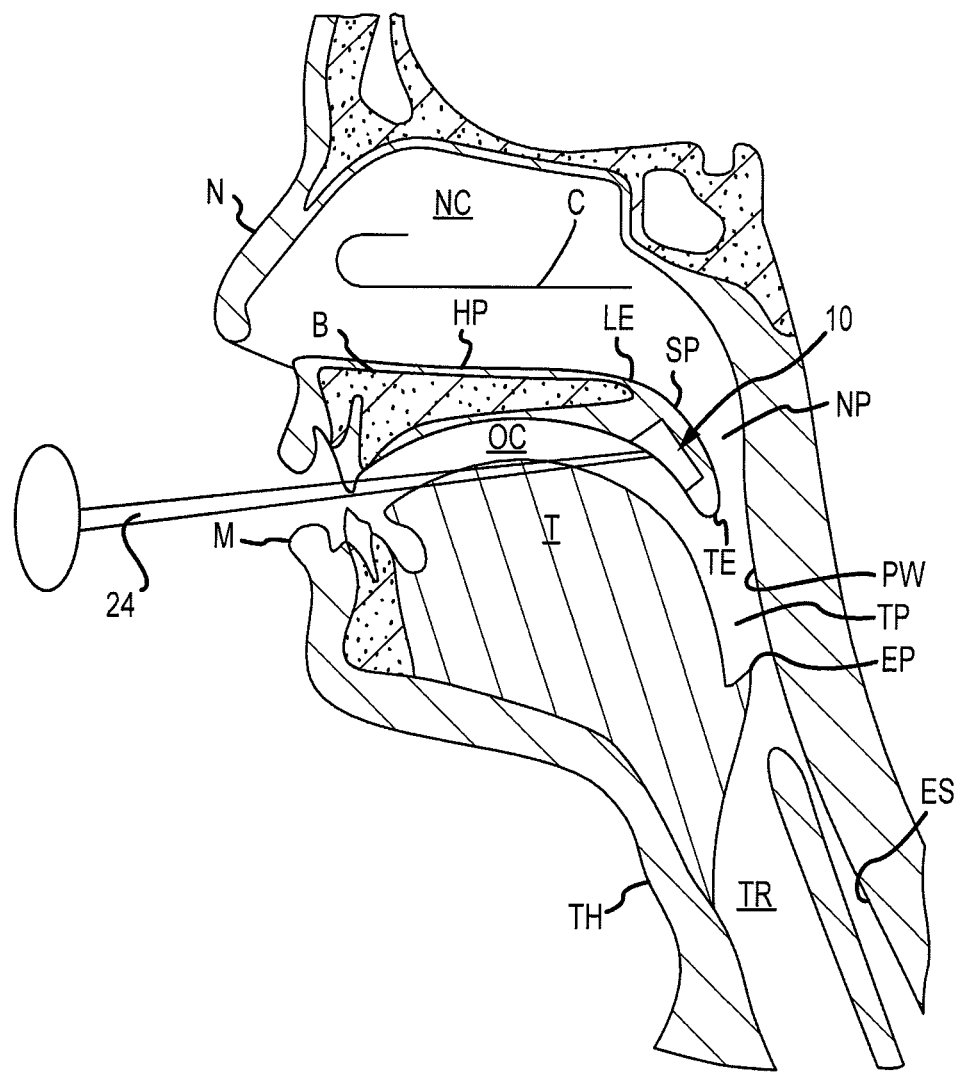
FIG. 9 illustrates a strip applicator for placing a snore strip properly on the soft palate.

FIG. 9 illustrates a strip applicator 24 for placing a snore strip 10 properly on the soft palate 12. Preferably the strip 10 (or strips, whether layered, certain portions more dissolvable than others, etc.) are positioned on a person's soft palate 12. This can be achieved via a person's fingers or through the use of an applicator 24 (otherwise described and illustrated.) The strip 10 is particularly suited to delivery of ingredients having activity in relation to snoring or apnea, by delivery to the mucosa of the throat, in particular at the soft tissue 12 in the pharyngeal region of the back of the throat, to keep the pharyngeal membranes moist and lubricated. The strip 10 is conformed as a relatively thin planar structure to facilitate desired rates of inter-oral dissolution. For example, in certain embodiments, a single strip 10 may be preferably no more than about 150 micron thick, more preferably in the range 100-400 micron thick, and in other embodiments may be over 500 microns in thickness. In other embodiments, however, the ability to layer strips 10 on top of one another provides for the manufacture and availability of strips 10 of more traditional thickness, such as those for example of the breath strips of Listerine, etc.

Reference herein to a strip 10 include any soluble prolonged release presentation of the composition which is conformable and is adapted to lie in a subject's mouth without causing obstruction or interfering with breathing, talking or swallowing or the like, or to conform to the surface of a subject's open skin or wound. Preferably the strip 10 comprises a flexible film or the like. In use, the strip 10 to be placed in a subject's mouth is intended to be placed at the back of the throat.

Components that can be included in strips 10 or associated with strips 10 in the various ways described herein include agents that may include additional active ingredients, including a plurality of active ingredients having an activity in relation to a particular condition or the throat or throat disorder, oral conditions, or conditions of snoring and/or sleep apnea, open skin or wound healing or repair agents and/or active ingredients having other desired activity. In still other embodiments, the use of additional ingredients may provide for chemical binding, and for example for the use of liposome technology, can be employed. In some embodiments of the invention a part or all of the active ingredients are encapsulated within encapsulation structures selected to provide the desired degree of adhesion to the mucous membranes of the throat, and adapted to release the active ingredients slowly over time in situ. These encapsulation structures may be distributed within the base material in the strip 10 composition. In one embodiment, the encapsulation-structures comprise multilamellar microparticles.

The strips 10 preferably have a surface that is antimicrobial in nature, such that such strips 10 assist in reducing the surface area in the mouth where noxious odors may arise due to the proliferation of foul smelling agents produced by bacteria that can survive in one's mouth. With possible breath freshening components added to the strip 10, morning breath and bad breath issues would be addressed, while the reduction in snoring would itself lead to a happier bedtime experience for both the wearer and his/her partner. One aspect of the present invention is directed to the novel combination of a specifically surface structured bioadhesively attachable, and in a preferred embodiment, dissolvable, strip 10 of material that persists in the mouth for at least one hour and preferably at least about 3 hours, so as to stiffen the tissue of the throat, specifically the soft palate 12, and thus reduce the occurrence of snoring. The ability to defeat the proliferation of bacteria in a person's mouth can significantly decrease the occurrence of so-called "morning breath".

Other embodiments employ differences in visual appearance to determine whether a strip 10 is placed properly; whether certain desired or undesired bacteria are present in the mouth, etc, and such effective means for determining the same include a film, coating or patch that includes one or more of the following characteristics: reflectance, retroreflectance, fluorescence, photoluminescent light transmission, color, tinting strength, and whiteness. In one particular embodiment, in addition to addressing snoring issues, certain embodiments may also assist in the detection of whether a person has a certain medical condition, such as strep throat. Thus, in one embodiment, the strip 10 changes color, expresses bioluminescence, etc. if there is strep bacteria present in a predetermined amount.

The foregoing describes numerous embodiments of an invention for an implant for the soft palate to alter a dynamic response of the soft palate. The invention is much less traumatic than prior surgical treatments. Further, the invention permits use of reversible procedures as well as procedures which can be selectively tuned both during surgery and post-operatively. Having described the invention, alternatives and embodiments may occur to one of skill in the art.

What is claimed is:

1. A method of treating snoring and/or obstructive sleep apnea in a subject in need of such treatment, comprising:
providing to the subject a buccal bioadhesive strip adapted to bind a mucosal membrane by applying said strip to the tissue of the soft palate to stiffen the tissue to reduce vibration, said strip comprising at least one coating layer having a surface topography for resisting bioadhesion, said at least one layer comprising a polymer, said coating layer having a pattern defined by a plurality of spaced apart features attached to or projected into a base surface, said plurality of features each having at least one microscale dimension and having at least one neighboring feature having a substantially different geometry, wherein an average spacing between adjacent ones of said features is between 0.5 and 5 μm in at least a portion of said coating layer, said coating layer resisting bioadhesion as compared to said base surface.

2. The method of claim 1, wherein the strip is non-biodegradable and is porous.

3. The method of claim 1, wherein the strip has a surface adapted to promote tissue in-growth.

4. The method of claim 1, wherein the strip is biodegradable and comprises a salt selected from the group consisting of a water soluble salt of a co-polymer of methyl vinyl ether and maleic acid, sodium hyaluronate, sodium alginate, and calcium alginate.

5. The method of claim 1, wherein said strip includes a bioadhesive selected from the group consisting of a carboxylated polymer, poly(acrylic acid) and crosslinked poly(acrylic acid).

6. The method of claim 1, wherein said strip does not result in permanent tissue changes that affect the physical characteristics of the soft palate.

7. The method of claim 1, wherein the strip is coated with one or more layers of crosslinked polyvinyl pyrrolidones and crosslinked polyacrylic acids.

8. The method as set forth in claim 1, wherein said strip has a first and second side, the first side having a bioadhesive that is adapted to bind to a mucosal membrane for at least 1 hour while inside a person's mouth, wherein said strip extends over a majority of the soft palate, and wherein said strip includes at least one polymer selected from the group consisting of pullulan, hydroxypropylmethyl cellulose, hydroxyethyl cellulose, hydroxypropyl cellulose, polyvinyl pyrrolidone, carboxymethyl cellulose, polyvinyl alcohol, sodium alginate, polyethylene glycol, tragacanth gum, guar gum, acacia gum, arabic gum, polyacrylic acid, methylmethacrylate copolymer, carboxyvinyl polymer, amylose, high amylose starch, hydroxypropylated high amylose starch, dextrin, pectin, chitin, chitosan, levan, elsinan, collagen, gelatin, zein, gluten, soy protein isolate, whey protein isolate, casein and mixtures thereof.

9. A method of treating snoring and/or obstructive sleep apnea in a subject in need of such treatment, comprising:
providing to a subject a buccal bioadhesive strip adapted to bind a mucosal membrane by applying said strip to the subject's tissue of the soft palate to stiffen the tissue and to reduce vibration of the tissue, the strip having a first and second side, the first side having a bioadhesive that is adapted to bind to a mucosal membrane for at least 1 hour while inside a person's mouth, wherein said strip has at least one layer comprising a polymer and extends over a majority of the soft palate, said second side resisting bioadhesion as compared to said first side and having a textured surface that has an anti-microbial characteristic comprising a textured surface having a topography that resists bioadhesion of bacteria present in a human's mouth, and wherein said bioadhesive is selected from the group consisting of a carboxylated polymer, poly(acrylic acid), crosslinked polyvinyl pyrrolidone, crosslinked poly(acrylic acid), polycarbophil, carbomer, and a water soluble salt of a co-polymer of methyl vinyl ether and maleic acid.

10. The method of claim 9, wherein the strip is non-biodegradable and is porous and includes breath freshening components.

11. The method of claim 9, wherein said strip comprises at least one polymer selected from the group consisting of a cellulose ether, methyl acrylate, hydroxypropyl methyl cellulose, hydroxypropyl cellulose, hydroxyethyl cellulose, methyl cellulose, carboxymethyl cellulose, polysulfone, polyvinyl alcohol, polyethylene oxide and polyethylene glycol.

12. The method of claim 9, wherein the strip is biodegradable and comprises a salt selected from the group consisting of a water soluble salt of a co-polymer of methyl vinyl ether and maleic acid, sodium hyaluronate, sodium alginate, and calcium alginate.

13. The method of claim 9, wherein said strip includes at least one polymer selected from the group consisting of pullulan, hydroxypropylmethyl cellulose, hydroxyethyl cellulose, hydroxypropyl cellulose, polyvinyl pyrrolidone, carboxymethyl cellulose, polyvinyl alcohol, sodium alginate, polyethylene glycol, tragacanth gum, guar gum, acacia gum, arabic gum, polyacrylic acid, methylmethacrylate copolymer, carboxyvinyl polymer, amylose, high amylose starch, hydroxypropylated high amylose starch, dextrin, pectin, chitin, chitosan, levan, elsinan, collagen, gelatin, zein, gluten, soy protein isolate, whey protein isolate, and casein, and wherein the strip comprises a hydrocolloid comprising at least between about 10% to about 50% by dry weight of the strip, said hydrocolloid selected from the group consisting of natural seaweeds, natural seed gum, natural plant exudates, natural fiber extracts, biosynthetic gums, gelatins, biosynthetic process starch or cellulosic materials, alginates, calcium alginate, marine colloids, natural gums, polysaccharides, sodium alginate, carrageenan, xanthan gum, gum acacia, gum arabic, guar gum, pullulan, agar, chitin, chitosan, pectin, karaya gum, zein, hordein, gliadin, carob meal, tragacanths, polysaccharides, maltodextrin, amylose, amylopectin, maize starch, potato starch, rice starch, tapioca starch, pea starch, sweet potato starch, barley starch, wheat starch, maize starch, dextrins, levan, elsinan, gluten, collagen, whey protein, casein, milk protein, soya protein, gelatine, colophony, and bees wax.

14. The method of claim 9, wherein said strip does not result in permanent tissue changes that affect the physical characteristics of the soft palate.

15. The method of claim 9, wherein said strip has an anti-microbial surface that reduces noxious odors arising from foul smelling agents produced by bacteria in the subject's mouth.

16. The method of claim 9, wherein said strip has no active drug.

17. The method of claim 9, wherein said strip has separate layers having different structural characteristics selected from the group of flexibility, dissolution rate, pliability and tensile strength.

18. The method of claim 9, wherein said strip comprises collagen selected from the group of collagen Type I, II and III.

19. The method of claim 9, wherein said strip is dissolvable and comprises a biodegradable polyester comprising polycaprolactone.

20. A method of treating snoring and/or obstructive sleep apnea in a subject in need of such treatment, comprising:
providing to a subject a buccal bioadhesive strip adapted to bind a mucosal membrane by applying said strip to the subject's tissue of the soft palate to stiffen the tissue and to reduce vibration of the tissue, the strip having a first and second side, the first side having a bioadhesive that is adapted to bind to a mucosal membrane for at least 1 hour while inside a person's mouth, wherein said strip has at least one layer comprising a polymer and extends over a majority of the soft palate, said second side resisting bioadhesion as compared to said first side and having at least one textured surface that has an anti-microbial characteristic that comprises a textured surface having a topography that resists bioadhesion of bacteria present in a human's mouth; wherein the strip is non-biodegradable and is porous, and wherein said bioadhesive is selected from the group consisting of a carboxylated polymer, poly (acrylic acid), crosslinked polyvinyl pyrrolidone, and crosslinked poly(acrylic acid); and wherein said strip does not result in permanent tissue changes that affect the physical characteristics of the soft palate.

* * * * *